US009387344B2

(12) United States Patent
Sgouros et al.

(10) Patent No.: US 9,387,344 B2
(45) Date of Patent: Jul. 12, 2016

(54) METHODS FOR DETERMINING ABSORBED DOSE INFORMATION

(75) Inventors: George Sgouros, Ellicott City, MD (US); Hong Song, Towson, MD (US); Andrew Prideaux, Baltimore, MD (US); Robert Hobbs, Baltimore, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 1440 days.

(21) Appl. No.: 12/514,853

(22) PCT Filed: Nov. 21, 2007

(86) PCT No.: PCT/US2007/085400
§ 371 (c)(1),
(2), (4) Date: Sep. 15, 2009

(87) PCT Pub. No.: WO2008/079569
PCT Pub. Date: Jul. 3, 2008

(65) Prior Publication Data
US 2010/0061607 A1 Mar. 11, 2010

Related U.S. Application Data

(60) Provisional application No. 60/860,315, filed on Nov. 21, 2006, provisional application No. 60/860,319, filed on Nov. 21, 2006.

(51) Int. Cl.
A61B 5/05 (2006.01)
A61N 5/10 (2006.01)
(Continued)

(52) U.S. Cl.
CPC ............ A61N 5/1031 (2013.01); A61B 6/5217 (2013.01); A61B 6/037 (2013.01)

(58) Field of Classification Search
CPC ..... A61N 5/1031; A61B 6/5217; A61B 6/037
See application file for complete search history.

(56) References Cited

U.S. PATENT DOCUMENTS 5,337,231 A 8/1994 Nowak et al.
6,090,365 A 7/2000 Kaminski et al.
(Continued)

FOREIGN PATENT DOCUMENTS

WO WO 99/62565 12/1999
WO WO 2004/067091 A1 * 8/2004

OTHER PUBLICATIONS

International Search Report of PCT/US2007/085400 dated Sep. 10, 2008.
(Continued)

Primary Examiner — James Kish
Assistant Examiner — Joseph M Santos Rodriguez
(74) Attorney, Agent, or Firm — DLA Piper LLP US

(57) ABSTRACT

The disclosure discusses methods for determining absorbed dose information. A tomography imaging device generates an anatomy image relating to anatomy of a particular patient. A tomography imaging device also generates multiple radioactivity images regarding radioactivity distribution of an internally administered pharmaceutical over time in the particular patient. The radioactivity images related to the radioactivity distribution over time are registered. Each radioactivity image is combined with each anatomy image to create activity images. A Monte Carlo simulation for each activity image is run to obtain absorbed dose-rate images of the pharmaceutical at multiple times. The absorbed dose-rate images are integrated over time to obtain a total absorbed dose image. The absorbed dose-rate images and the total absorbed dose image are used to obtain a biologically effective dose (BED) image. The BED image is used to obtain an equivalent uniform does (EUD) of BED values for a chosen anatomical region.

8 Claims, 26 Drawing Sheets

(51) Int. Cl.
*A61B 6/00* (2006.01)
*A61B 6/03* (2006.01)

(56) References Cited

U.S. PATENT DOCUMENTS

| | | | |
|---|---|---|---|
| 6,251,362 | B1 | 6/2001 | Wahl et al. |
| 6,560,311 | B1 | 5/2003 | Shepard |
| 6,694,298 | B1 | 2/2004 | Teagarden et al. |
| 7,046,762 | B2 | 5/2006 | Lee |
| 7,668,662 | B2 | 2/2010 | Kroll et al. |
| 7,787,669 | B2 * | 8/2010 | Botterweck et al. ......... 382/128 |
| 8,663,083 | B2 | 3/2014 | Georgi et al. |
| 2002/0046010 | A1 | 4/2002 | Wessol et al. |
| 2003/0219098 | A1 | 11/2003 | McNutt et al. |
| 2004/0131587 | A1 | 7/2004 | Thomas et al. |
| 2004/0213737 | A1 | 10/2004 | Huang et al. |
| 2005/0028869 | A1 | 2/2005 | Roth et al. |
| 2005/0288869 | A1 | 12/2005 | Kroll et al. |
| 2006/0025824 | A1 | 2/2006 | Freeman et al. |
| 2006/0050839 | A1 | 3/2006 | Balan et al. |
| 2006/0058966 | A1 | 3/2006 | Bruckner |
| 2008/0247510 | A1 | 10/2008 | Gertner et al. |
| 2009/0154644 | A1 | 6/2009 | Nord et al. |
| 2009/0316858 | A1 | 12/2009 | Nord |
| 2010/0081857 | A1 | 4/2010 | Georgi et al. |
| 2010/0232572 | A1 | 9/2010 | Nord et al. |
| 2011/0091014 | A1 | 4/2011 | Siljamaki |

OTHER PUBLICATIONS

Elienne Garin et al., "Effect of a 188 Re-SSS lipiodol/131I-lipidol mixture, 188 Re-SSS lipiodol alone or 131I-lipiodol alone on the survival of rats with hepatocellular carcinoma", Nuclear Medicine Communications, vol. 27, No. 4, pp. 363-369, Apr. 2006.
A. Lechner et al., "Targeted Radionuclide therapy: theoretical study of the relationship between tumour control probability and tumour radius for a 32 P/33 P radionuclide cocktail", Physics in Medicine and Biology, vol. 53, No. 7, pp. 1961-1974, Mar. 18, 2008.
Linda Villard et al., "Cohort Study of Somatostatin-Based Radiopeptide Therapy With [90Y-DOTA]-TOC Versus [90Y-DOTA]-TOC Plus [177Lu-DOTA]-TOC in Neuroendocrine Cancers", Journal of Clinical Oncology, vol. 30, No. 10, pp. 1100-1106, Apr. 1, 2012.
Greg L. Plosker et al., "Rituximab: A Review of its Use in Non-Hodgkin's Lymphoma and Chronic Lymphocytic Leukaemia", Drugs, vol. 63, No. 8, pp. 803-843 (2003).
Gillian M. Keating. "Spotlight on Rituximab in Chronic Lymphocytic Leukemia, Low-Grade or Follicular Lymphoma, and Diffuse Large B-Cell Lymphoma", BioDrugs, vol. 25, No. 1, pp. 55-61, Feb. 2011.
Thomas E. Witzig, "Treatment recommendations for Radioimmunotherapy in Follicular Lymphoma: A Consensus Conference Report", Leuk. Lymphoma, vol. 52, No. 7, pp. 1188-1199, Jul. 2011.
Peter Johnson et al., "The Mechanisms of Action of Rituximab in the Elimination of Tumor Cells", Seminars in Oncology, vol. 30, No. 1, Suppl 2, pp. 3-8, Feb. 2003.
Oliver W. Press et al., "Treatment of Refractory Non-Hodgkins's Lymphoma with Radiolabeled MB-1 (anti-CD37) Antibody", Journal of Clinical Oncology, vol. 7, No. 8, pp. 1027-1038, Aug. 1989.
Oliver W. Press et al., "Phase II Trial of 131I-B1 (anti-CD20) Antibody Therapy with Autologous Stem Cell Transplantation for Relapsed B Cell Lymphomas", The Lancet, vol. 346, No. 8971, pp. 336-340, Aug. 5, 1995.
E. Frey et al., "Estimation of Post-Therapy Marrow Dose Rate in Myeloablative Y-90 Ibritumomab Tiuxetan Therapy", J. Nucl. Med., vol. 47, No. Suppl 1, pp. 156P (2006).
Richard Wahl et al., "Organ Dosimetry Dose Escalation of Yttrium 90 Ibritumomab Tiuxetan radioimmunotherapy (90Y IT) with Stem Cell Transplantation (ASCT) in Patients with Non-Hodgkin's Lymphoma (NHL)", The Journal of Nuclear Medicine, vol. 47, Supplement 1, pp. 97P (2006) (2 pages).

Ian M. Besse et al., "Modeling Combined Radiopharmaceutical Therapy: A Linear Optimization Framework", Technology in Cancer Research and Treatment, vol. 8, No. 1, pp. 51-60, Feb. 2009.
Hanan Amro et al., "Methodology to Incorporate Biologically Effective Dose and Equivalent Uniform Dose in Patient-Specific 3-Dimensional Dosimetry for Non-Hodgkin Lymphoma Patients Targeted with 131I-Tositumomab Therapy", The Journal of Nuclear Medicine, vol. 51, No. 4, pp. 654-659, Apr. 2010.
Robert F. Hobbs et al., "A Treatment Planning Method for Sequentially Combining Radiopharmaceutical Therapy and External radiation Therapy", Int. J. Radiation Oncology Biol. Phys., vol. 80, No. 4, pp. 1256-1262, (2011).
Sebastien Baechler et al., "Extension of the Biological Effective Dose to the MIRD Schema and Possible Implications in Radionuclide Therapy Dosimetry", Med. Phys., vol. 35, No. 3, pp. 1123-1134, Mar. 2008.
Amr Aref et al., "Radiobiological Characterization of Two Human Chemotherapy-Resistant intermediate Grade Non-Hodgkin's Lymphoma Cell Lines", Radiation Oncology Investigations, vol. 7, pp. 158-162 (1999).
J. Van Dyk et al., "Radiation-induced Lung Damage: Dose-Time-Fractionation Considerations", Radiotherapy and Oncology, vol. 14, pp. 55-69 (1989).
Bin He et al., "Comparison of Organ Residence time estimation Methods for Radioimmunotherapy Dosimetry and Treatment Planning—Patient Studies", Med. Phys., vol. 36, No. 5, pp. 1595-1601, May 2009.
Sunil Krishnan et al., "Conformal Radiotherapy of the Dominant Liver Metastasis; A Viable Strategy for Treatment of Unresectable Chemotherapy Refractory Colorectal Cancer Liver Metastases", American Journal of Clinical Oncology, vol. 29, No. 6, pp. 562-567, Dec. 2006.
Sebastien Baechler et al., "Three-Dimensional Radiobiological Dosimetry of Kidneys for Treatment Planning in Peptide Receptor Radionuclide Therapy" Med. Phys., vol. 29, No. 10, pp. 6118-6128, Oct. 2012.
Massimiliano Pacilio et al., "A Theoretical Dose-Escalation Study Based on Biological Effective Dose in Radioimmunotherapy with (90)Y-ibritumomab Tiuxetan (Zevalin)", Eur. J. Nucl. Med. Mol. Imaging, vol. 37, pp. 862-873, (2010).
J. Kotzerke et al., "Radioimmunoconjugates in Acute Leukemia Treatment: The Future is Radiant", Bone Marrow Transplantation, vol. 36, pp. 1021-1026, Oct. 10, 2005.
J.A. O'Donoghue et al., "Relationships Between Tumor Size and Curability for Uniformly Targeted Therapy with Beta-Emitting Radionuclides", The Journal of Nuclear Medicine, vol. 36, No. 10, pp. 1902-1909, Oct. 1995.
Jolanta Kunikowska et al., "Clinical Results of Radionuclide Therapy of Neuroendocrine Tumours with 90Y-DOTATATE and Tandem 90Y/177 Lu-DOTATATE: Which is Better Therapy Option?", Eur. J. Nucl. Med. Mol. Imaging, vol. 38, pp. 1788-1797, May 7, 2011.
Mark T. Madsen et al., "Potential Increased Tumor-Dose Delivery with Combined 131I-MIBG and 90Y-DOTATOC Treatment in Neuroendocrine Tumors: A Theoretic Model", The Journal of Nuclear Medicine, vol. 47, No. 4, pp. 660-667, Apr. 2006.
Thomas A. Davis et al., "The Radioisotope Contributes Significantly to the Activity of Radioimmunotherapy", Clinical Cancer Research, vol. 10, pp. 7792-7798, Dec. 7, 2004.
Thomas E. Witzig et al., "Randomized Controlled Trial of Yttrium-90-Labeled Ibritumomab Tiuxetan Radioimmunotherapy Versus Rituximab Immunotherapy for Patients With Relapsed or Refactory Low-Grade, Follicular, or Transformed B-Cell non-Hodgkin's Lymphoma", Journal of Clinical Oncology, vol. 20, No. 10, pp. 2453-2463, May 15, 2002.
Oliver W. Press et al., "Radiolabeled-Antiboy Therapy of B-Cell Lymphoma with Autologous Bone Marrow Support", The New England Journal of Medicine, vol. 329, No. 17, pp. 1219-1224, Oct. 21, 1993.
Ajay K. Gopal et al., "High-Dose [131I] Tositumomab (anti-CD20) Radioimmunotherapy and Autologous Hematopoietic Stem-Cell Transplantation for Adults ≥ 60 Years Old With Relapsed or Refac-

(56) References Cited

OTHER PUBLICATIONS tory B-Cell Lymphoma", Journal of Clinical Oncology, vol. 25, No. 11, pp. 1396-1402, Apr. 10, 2007.
Ajay K. Gopal et al., "High-Dose Radioimmunotherapy Versus Conventional High-Dose Therapy and Autologous Hematopoietic Stem Cell Transplantation for Relapsed Follicular Non-Hodgkin Lymphoma: A Multivariable Cohort Analysis", Blood, vol. 102, pp. 2351-2357, Oct. 1, 2003.
Amrita Krishnan et al., "Phase II Trial of a Transplantation Regimen of Yttrium-90 Ibritumomab Tiuxetan and High-Dose Chemotherapy in Patients with Non-Hodgkin's Lymphoma", Journal of Clinical Oncology, vol. 26, No. 1, pp. 90-95, Jan. 1, 2008.
Jane N. Winter et al., "Yttrium-90 Ibritumomab Tiuxetan Doses Calculated to Deliver up to 15 Gy to Critical Organs May Be Safely Combined With High-Dose BEAM and Autologous Transplantation in Relapsed or Refractory B-Cell Non-Hodgkin's Lymphoma", Journal of Clinical Oncology, vol. 27, No. 10, pp. 1653-1659, Apr. 1, 2009.
Hong Song et al., "Therapuetic Potential of 90Y- and 131I-Labeled Anti-CD20 Monoclonal Antibody in Treating Non-Hodgkin's Lymphoma with Pulmonary Involvement: A Monte Carlo-Based Dosimetric Analysis", The Journal of Nuclear Medicine, vol. 48, No. 1, pp. 150-157, Jan. 2007.
Gregory A. Wiseman et al., "Phase I/II 90Y-Zevalin (Yttrium-90 Ibritumomab Tiuxetan, IDEC-Y2B8) Radioimmunotherapy Dosimetry Results in Relapsed or Refractory Non-Hodgkin's Lymphoma", European Journal of Nuclear Medicine, vol. 27, No. 7, pp. 766-777, Jul. 2000.
Raffaella Barone et al., "Patient-Specific Dosimetry in Predicting Renal Toxicity with 90Y-DOTATOC: Relevance of Kidney Volume and Dose Rate in Finding a Dose-Effect Relationship", The Journal of Nuclear Medicine, vol. 46, No. 1 (Suppl), pp. 99S-106S, Jan. 2005.
Barry W. Wessels et al., "MIRD Pamphlet No. 20: The Effect of Model Assumptions on Kidney Dosimetry and Response—Implications for Radionuclide Therapy", The Journal of Nuclear Medicine, vol. 49, No. 11, pp. 1884-1899, Nov. 2008.
Lidia Strigari et al., "Efficacy and Toxicity Related to Treatment of Hepatocellular Carcinoma with 90Y-SIR Spheres: Radiobiologic Considerations", The Journal of Nuclear Medicine, vol. 51, No. 9, pp. 1377-1385, Sep. 2010.
Yuni K. Dewaraja et al., "131I-Tositumomab Radioimmunotherapy: Initial Tumor Dose—Response Results Using 3-Dimensional Dosimetry Including Raditobiologic Modeling", The Journal of Nuclear Medicine, vol. 51, No. 7, pp. 1155-1162, Jul. 2010.
Mahila E. Ferrari et al., "3D Dosimetry in Patients with Early Breast Cancer Undergoing Intraopeative Avidination for Radionuclide Therapy (IART) Combined with External Beam Radiation Therapy", Eur. J. Nucl. Med. Mol. Imaging, vol. 39, pp. 1702-1711 (2012).
Marta Cremonesi et al., "Radioembolisation with 90Y-Microspheres: Dosimetric and Radiobiological Investigation for Multi-Cycle Treatment", Eur. J. Nucl. Med. Mol. Imaging, vol. 35, pp. 2088-2096 (2008).
Roger W. Howell et al., "Application of the Linear-Quadratic Model to Radioimmunotherapy: Further Support for the Advantage of Longer-Lived Radionuclides", The Journal of Nuclear Medicine, vol. 35, No. 11, pp. 1861-1869, Nov. 1994.
Siyada N.F. Rizvi et al., "Biodistribution, Radiation Dosimetry and Scouting of 90Y-Ibritumomab Tiuxetan Therapy in Patients with Relapsed B-Cell Non-Hodgkin's Lymphoma Using 89Zr-Ibritumomab Tiuxetan and PET", Eur. J. Nucl. Med. Mol. Imaging, vol. 39, pp. 512-520 (2012).
George Sgouros et al., "Patient-Specific, 3-Dimensional Dosimetry in Non-Hodgkin's Lymphoma Patients Treated with 131I-Anti-B1 Antibody: Assessment of Tumor Dose—Response", The Journal of Nuclear Medicine, vol. 44, No. 2, pp. 260-268, Feb. 2003.
Heather A. Jacene et al., "Comparison of 90Y-Ibritumomab Tiuxetan and 131I-Tositumomab in Clinical Practice", The Journal of Nuclear Medicine, vol. 48, No. 11, pp. 1767-1776, Nov. 2007.
U.S. Appl. No. 12/687,670.
U.S. Appl. No. 12/820,852.

Oliver W. Press et al., "A Phase I/II Trial of Iodine-131-tositumomab (anti-CD20),etoposide, cyclophosphamide, and Autologous Stem Cell Transplantation for Relapse B-Cell Lymphomas", Blood, vol. 96, No. 9, pp. 2934-2942, Nov. 1, 2000.
B. Emami et al., "Tolerance of Normal Tissue to Therapeutic Irradiation", Int. J. Radiation Oncology Biol. Phys., vol. 21, pp. 109-122 (1991).
Roger Dale et al., "The Radiobiology of Conventional Radiotherapy and Its Application to Radionuclide Therapy", Cancer Biotherapy & Radiopharmaceuticals, vol. 20, No. 1, pp. 47-51 (2005).
Roger Dale, "Use of the Linear-Quadratic Radiobiological Model for Quantifying Kidney Response in Targeted Radiotherapy", Cancer Biotherapy & Radiopharmaceuticals, vol. 19, No. 3, pp. 363-370 (2004).
Joseph A. O'Donoghue, "Implications of Nonuniform Tumor Doses for Radioimmunotherapy", The Journal of Nuclear Medicine, vol. 40, No. 8, pp. 1337-1341, Aug. 1999.
MIRD Pamphlet No. 21: A Generalized Schema for Radiopharmaceutical Dosimetry—Standaradization of Nomenclature, The Journal of Nuclear Medicine, vol. 50, No. 3, pp. 477-484, Mar. 2009.
Bin He et al., "A Monte Carlo and Physical Phantom Evaluation of Quantitative In-111 SPECT", Physics in Medicine Biology, vol. 50, pp. 4169-4185 (2005).
H. Malcolm Hudson et al., "Accelerated Image Reconstruction Using Ordered Subsets of Projection Data", IEEE Transactions on Medical Imaging, vol. 13, No. 4, pp. 601-609, Dec. 1994.
Dan J. Kadrmas et al., "Fast Implementations of Reconstruction-Based Scatter Compensation in Fully 3D SPECT Image Reconstruction", Phys. Med. Biol., vol. 43, No. 4, pp. 857-873, Apr. 1998.
Robert F. Hobbs et al., "Arterial Wall Dosimetry for Non-Hodgkin Lymphoma Patients Treated with Radioimmunotherapy", The Journal of Nuclear Medicine, vol. 51, No. 3, pp. 368-375, Mar. 2010.
Robert F. Hobbs et al., "$^{124}$I PET-Based 3D-RD Dosimetry for a Pediatric Thyroid Cancer Patient: Real-Time Treatment Planning and Methodologic Comparison", The Journal of Nuclear Medicine, vol. 50, No. 11, pp. 1844-1847, Nov. 2009.
Andrew R. Prideaux et al., "Three-Dimensional Radiobiologic Dosimetry: Application of Radiobiologic Modeling to Patient-Specific 3-Dimensional Imaging-Based Internal Dosimetry", The Journal of Nuclear Medicine, vol. 48, No. 6, pp. 1008-1016, Jun. 2007.
John F. Fowler, "The Linear-Quadratic Formula and Progress in Fractionated Radiotherapy", The British Journal of Radiology, vol. 62, No. 740, pp. 679-694, Aug. 1989.
William T. Millar, "Application of the Linear-Quadratic Model with Incomplete Repair to Radionuclide Directed Therapy", The British Journal of Radiology, vol. 64, No. 759, pp. 242-251, Mar. 1991.
D.J. Brenner et al., "The Linear-Quadratic Model and Most Other Common Radiobiological Models Result in Similar Predictions of Time-Dose Relationships", Radiation Research, vol. 150, pp. 83-91 (1998).
Robert F. Hobbs et al., "Calculation of the Biological Effective Dose for Piecewise Defined Dose-Rate Fits", Med. Phys., vol. 36, No. 3, pp. 904-907, Mar. 2009.
R. G. Dale, "The Application of the Linear-Quadratic Dose-Effect Equation to Fractionated and Protracted Radiotherapy", The British Journal of Radiology, vol. 58, No. 690, pp. 515-528, Jun. 1985.
R. K. Bodey et al., "Combining Dosimetry for Targeted Radionuclide and External Beam Therapies Using the Biologically Effective Dose", Cancer Biotherapy & Radiopharmaceuticals, vol. 18, No. 1, pp. 89-97 (2003).
Rachel K. Bodey et al,. "Application of the Linear-Quadratic Model to Combined Modality Radiotherapy", Int. J. Radiation Oncology Biol. Phys., vol. 59, No. 1, pp. 228-241 (2004).
D. J. Brenner et al., "Conditions for the Equivalence of Continuous to Pulsed Low Dose Rate Brachytherapy", Int. J. Radiation Oncology Biol. Phys., vol. 20, pp. 181-190, Jan. 1991.
C. Chiesa et al., "A Practical Dead Time Correction Method in Planar Activity Quantification for Dosimetry During Radionuclide Therapy", The Quarterly Journal of Nuclear Medicine and Molecular Imaging, vol. 53, No. 6, pp. 5658-5670, Dec. 2009.

(56) References Cited

OTHER PUBLICATIONS

G. Delpon et al., "Correction of Count Losses Due to Deadtime on a DST-Xli (SMVi-GE) Camera During Dosimetric Studies in Patients Injected with Iodine-131", Physics in Medicine and Biology, vol. 47, pp. N79-N90 (2002).

James A. Sorenson et al., "Methods of Correcting Anger Camera Deadtime Losses", Journal of Nuclear Medicine, vol. 17, No. 2, pp. 137-141 (1976).

Kenneth R. Zasadny et al., "Dead Time of an Anger Camera in Dual-Energy-Window-Acquisition Mode", Med. Phys., vol. 20, No. 4, pp. 1115-1120, Jul./Aug. 1993.

Indra J. Das et al., "Intensity-Modulated Radiation Therapy Dose Prescription, Recording, and Delivery: Patterns of Variability Among Institutions and Treatment Planning Systems", JNCI, vol. 100, Issue 5, pp. 300-307, Mar. 5, 2008.

David M. Loeb et al., "Dose-finding study of 153Sm-EDTMP in Patients with Poor-Prognosis Osteosarcoma", Cancer, vol. 115, No. 11, pp. 2514-2522, Jun. 1, 2009.

David M. Loeb et al. "Tandem Dosing of Samarium-153 Ethylenediamin Tetramethylene Phosphoric Acid with Stem Cell Support for Patients with High Risk Osteosarcoma", Cancer, pp. 5470-5478, Dec. 1, 2010.

Pete Anderson et al., "Samarium Lexidronam (153Sm-EDTMP): Skeletal Radiation for Osteoblastic Bone Metastases and Osteosarcoma", Expert Rev Anticancer Ther., vol. 7, No. 11, pp. 1517-1527, Nov. 2007.

I. Resche et al., "A Dose-Controlled Study of 153Sm-Ethylenediaminetetramethylenephosphonate (EDTP) in the Treatment of Patients with Painful Bone Metastases", European Journal of Cancer, Vo. 33, No. 10, pp. 1583-1591, Sep. 1997.

Oliver Sartor et al., "Safety and Efficacy of Repeat Administration of Samarium Sm-153 Lexidronam to Patients with Metastatic Bone Pain", Cancer, vol. 109, No. 3, pp. 637-643, Feb. 1, 2007.

Oliver Sartor et al., Samarium-153-Lexidronam Complex for Treatment of Painful Bone Metastases in Hormone-Refractory Prostate Cancer, Urology, vol. 63, No. 5, pp. 940-945, May 2004.

Aldo N. Serafmi et al. Palliation of Pain Associated with Metastatic Bone cancer Using Samarium-153 Lexidronam: A Double-Blind Placebo-Controlled Clinical Trial, Journal of Oncology, vol. 16, No. 4, pp. 1574-1581, Apr. 1998.

Peter M. Anderson et al., "Gemcitabine Radiosensitization After High-Dose Samarium for Osteoblastic Osteosarcoma", Clin Cancer Res., vol. 11, No. 19, pp. 6895-6900, Oct. 1, 2005.

Peter M. Anderson et al., High-Dose Samarium-153 Ethylene Diamine Tetramethylene Phosphonate: Low Toxicity of Skeletal Irradiation in Patients with Osteosarcoma and Bone Metastases, Journal of Clinical Oncology, vol. 20, No. 1, pp. 189-196, Jan. 1, 2002.

H. Malcolm Hudson et al., "Accelerated Image-Reconstruction Using Ordered Subsets of Projection Data", IEEE T. Med. Imaging, vol. 13, No. 4, pp. 601-609, Dec. 1994.

Robert F. Hobbs et al., "A Gamma Camera Count Rate Saturation Correction Method for Whole-Body Planar Imaging", Physics in Medicine and Biology, vol. 55, pp. 817-831, (2010).

T.S. Kehwar, "Analytical Approach to Estimate Normal Tissue Complication Probability Using Best Fit of Normal Tissue Tolerance Doses into the NTCP Equation of the Linear Quadratic Model", J. Cancer Res. Ther., vol. 1, No. 3, pp. 168-179, Sep. 2005.

Rachel K. Bodey et al., "Spatial Aspects of Combined Modality Radiotherapy", Radiotherapy and Oncology, Vo. 77, No. 3, pp. 301-309, Dec. 2005.

Yong Du et al., "Partial Volume Effect Compensation for Quantitative Brain SPECT Imaging", IEEE Transactions on Medical Imaging, vol. 24, No. 8, pp. 969-976, Aug. 2005.

Edgardo Browne et al., "Table of Radioactive Isotopes", John Wiley & Sons, pp. 90-1-90-4 and 111-1-111-4, Copyright 1986.

Thomas Bortfeld et al, "Image-Guided IMRT", Springer, pp. V-XII, and 1-460, Copyright 2006.

Mihael Ankerst et al., "3d Shape Histograms for Similarity Search and Classification in Saptial Databases", Proc. 6th International Symposium on Spatial Databases (SSD'99), Hong Kong, China, Lecture Notes in Computer Science, pp. 207-226, Jul. 1999.

Paul J. Besl, "Triangles as a Primary Representation", Object Representation in Computer Vision, Lecture Notes in Computer Science, vol. 994, pp. 191-206 (1995).

Cha Zhang, "Project—3D Model Retrieval", http://amp.ece.cmu.edu/projects/3DModelRetrieval/, Nov. 2, 2002 (6 pages).

Ding-Yun Chen et al., "On Visual Similarity Based 3D Model Retrieval", Computer Graphics Forum (Eurographics 2003), vol. 22, No. 3, pp. 223-232 (2003).

R.E. Drzymala, "Dose-Volume Histograms", International Journal of Radiation Oncology, Biology, Physics, vol. 21, No. 1, pp. 71-78 (1991).

Andrea Frome et al., "Recognizing Objects in Range Data Using Regional Point Descriptors", Computer Vision (ECCV 2004), Lecture Notes in Computer Science, vol. 3023, pp. 224-237 (2004).

Thomas Funkhouser et al., "A Search Engine for 3D Models", ACM Transactions on Graphics (TOG), vol. 22, Issue 1, pp. 83-105, Jan. 2003.

Timothy Gatzke et al., "Curvature Maps for Local Shape Comparison", In Shape Modeling International, pp. 244-253 (2005).

James Gain et al., "Fast Polygon Mesh Querying by Example", AMC SIGGRAPH'99 Conference Abstracts and Applications, pp. 241, Aug. 1999.

Berthold K.P. Horn, "Extended Gaussian Images", Proceedings of the IEEE, vol. 72, No. 12, pp. 1671-1686, Dec. 1984.

Andrew Edie Johnson et al., "Efficient Multiple Model Recognition in Cluttered 3-D Scenes", Proc. IEEE Conference on Computer Vision and Pattern, pp. 671-677 (1998).

A.E. Johnson et al., "Using Spin-Images for Efficient Multiple Model Recognition in Cluttered 3D Scenes", IEEE Transactions on Pattern Analysis and Machine Intelligence, vol. 21, Issue 5, pp. 433-449, May 1999.

Michael Kazhdan et al., "A Reflective Symmetry Descriptor", ECCV 2002, LNCS 2351, pp. 642-656 (2002).

Robert Osada et al., "Matching 3D Models with Shape Distributions", International Conference on Shape Modeling and Applications (SMI 2001), pp. 154-166, May 2001.

Robert Osada et al., "Shape Distributions", ACM Transactions on Graphics, vol. 21, No. 4, p. 807-832, Oct. 2002.

"3D Model Search Engine", http://shape.cs.princeton.edu/search.html, Nov. 2001 (1 page).

Yossi Rubner et al., "The Earth Mover's Distance as a Metric for Image Retrieval", International Journal of Computer Vision, vol. 40, No. 2, pp. 99-121 (2000).

Dietmar Saupe et al., "3D Model Retrieval with Spherical Harmonics and Moments", DAGM 2001, LNCS 2191, pp. 392-397 (2001).

Sen Wang et al., "Conformal Geometry and its Applications on 3D Shape Matching, Recognition, and Stitching", IEE Transactions on Pattern Analysis and Machine Intellience, vol. 29, No. 7, pp. 1209-1220, Jul. 2007.

Jaun Zhang et al., "Retrieving Articulated 3-D Models Using Medial Surfaces and Their Graph Spectra", EMMCVPR 2005, LNCS 3757, pp. 285-300 (2005).

Avraham Eisbruch et al., "Multi-Institutional Trial of Aaccellerated Hypofractionated Intensity-Modulated Radiation Therapy for Early-Stage Oropharyngeal Cancer (RTOG 00-22)", International Journal of Radiation Oncology, Biology, Physics, vol. 76, No. 5, pp. 1333-1338, Apr. 2010.

Binbin Wu et al., "Patient Geometry-Driven Information retrieval for IMRT Treatment Plan Quality Control", Med. Phys., vol. 36, No. 12, pp. 5497-5505, Dec. 2009.

Mark S. Kaminiski et al., "Pivotal Study to Iodine I 131 Tositumomab for Chemotherapy-Refractory Low-Grade or Transformed Low-Grade B-Cell Non-Hodgkin's Lymphomas", Journal of Clinical Oncology., vol. 19, No. 19, pp. 3918-3928, Oct. 1, 2001.

Julie M. Vase et al., "Multicenter Phase II Study of Iodine-131 Tositumomab for Chemotherapy-Relapsed/Refractory Low-Grade and Transformed Low-Grade B-Cell Non-Hodgkin's Lymphomas", Journal of Clinical Oncology, vol. 18, No. 6, pp. 1316-1323, Mar. 2000.

Kenneth F. Koral et al., "Volume Reduction Versus Radiation Dose for Tumors in Previously Untreated Lymphoma Patients Who

(56) References Cited

OTHER PUBLICATIONS

Received Iodine-131 Tositumomab Therapy: Conjugate Views With a Hybrid Method", Cancer, vol. 94, No. 4 (Suppl) pp. 1258-1263, Feb. 15, 2002.

Susan J. Knox et al., "Yttrium-90-Labeled Anti-CD20 Monoclonal Therapy of Recurrent B-Cell Lymphoma", Clinical Cancer Research, vol. 2, pp. 457-470, Mar. 1996.

Mark S. Kaminski et al., "Radioimmunotherpay of B-cell lymphoma with [131I]anti-B1 (anti-CD20) antibody", The New England Journal of Medicine, vol. 329, No. 7, pp. 459-465, Aug. 12, 1993.

Mark S. Kaminski et al., "Radioimmunotherapy with iodine 131I tositumomab for relapsed or refractory B-cell non-Hodgkin lymphoma: updated results and long-term follow-up of the University of Michigan experience", Blood, vol. 96, No. 4, pp. 1259-1266, Aug. 15, 2000.

Mark S. Kaminski et al., "131I-tositumomab therapy as initial treatment for follicular lymphoma", The New England Journal of Medicine, vol. 352, No. 5, pp. 441-449, Feb. 3, 2005.

Thomas E. Witzig et al., "Treatment with Ibritumomab Tiuxetan Radioimmunotherapy in Patients with Rituximab-Refractory Follicular Non-Hodgkin's Lymphoma", Journal of Clinical Oncology, vol. 20, No. 15, pp. 3262-3269, Aug. 1, 2002.

Raymond R. Raylman et al., "Magnetically enhanced radionuclide therapy", Journal of Nuclear Medicine, vol. 35, No. 1, pp. 157-163, Jan. 1994.

Donald J. Buchsbaum et al., "Improved delivery of radiolabeled anti-B1 monoclonal antibody to Raji lymphoma xenografts by predosing with unlabeled anti-B1 monoclonal antibody", Cancer Research, vol. 52, pp. 637-642, Feb. 1, 1992.

Kenneth F. Koral, "CT-SPECT fusion plus conjugate views for determining dosimetry in iodine-131-monoclonal antibody therapy of lymphoma patients", The Journal of Nuclear Medicine, vol. 35, No. 10, pp. 1714-1720, Oct. 1994.

T.E. Wheldon et al., "The curability of tumours of differing size by targeted radiotherapy using 131I or 90Y", Radiotherapy and Oncology, vol. 21, pp. 91-99. (1991).

Raymond R. Raylman et al., "Magnetically-enhanced radionuclide therapy (MERiT): in vitro evaluation", Int. J. Radiation Oncology Biol. Phys., vol. 37, No. 5, pp. 1201-1206 (1997).

Raymond R. Raylman et al., "Magnetically enhanced protection of bone marrow from beta particles emitted by bone-seeking radionuclides: theory of application", Medical Physics, vol. 22, No. 8, pp. 1285-1292, Aug. 1995.

Raya S. Brown et al., "Intra-tumoral microdistribution of 131I-labelled in patients with B-cell lymphoma following radioimmunotherapy", Nuclear Medicine & Biology, vol. 24, pp. 657-663 (1997).

S. Piantadosi et al., "Practical implementation of a modified continual reassessment method for dose-finding trials", Cancer Chemother Phamacol, vol. 41, pp. 429-436 (1998).

G.A. Wiseman et al., "Radiation dosimetry results from a Phase II trial of ibritumomab tiuxetan (Zevalin) radioimmunotherapy for patients with non-Hodgkin's lymphoma and mild thrombocytopenia", Cancer Biotherapy & Radiopharmaceuticals, vol. 18, No. 2, pp. 165-178. Apr. 2003.

Richard L. Wahl et al., "Patient-Specific Whole-Body Dosimetry: Principles and a Simplified Method for Clinical Implementation", The Journal of Nuclear Medicine, vol. 39, No. 8 (Suppl), pp. 14S-20S, Aug. 1998.

Jorg. Bohsung, et al, "IMRT Treatment Planning—A Comparative Inter-System and Inter-Centre Planning Exercise of the QUASIMODO Group," Radiotherapy and Oncology, vol. 76, pp. 354-361 (2005).

Anders B. Jensen, et al, "Influence of Late Side-Effects Upon Daily Life After Radiotherapy for Laryngeal and Pharyngeal Cancer," Acta Oncologica, vol. 33, pp. 487-491 (1994).

Q. Wu et al., "Algorithms and Functionality of an Intensity Modulated Radiotherapy Optimization System," Med. Phys., vol. 27, pp. 701-711 (2000).

A. Brahme, "Optimization of Stationary and Moving Beam Radiation Therapy Techniques," Radiother Oncol., vol. 12, pp. 129-140 (1988).

R. Lu et al., "Reduced-Order Parameter Optimization for Simplifying Protate IMRT Planning," Phys. Med. Biol., vol. 52, pp. 848-870 (2007).

H. T. Chung et al., "Can All Centers Plan Intensity-Modulated Radiotherapy (IMRT) Effectively? An External Audit of Dosimetric Comparisons Between Three-Dimensional Conformal Radiotherapy and IMRT for Adjuvant Chemoradiation for Gastric Cancer," Int. J. Radiat. Oncol. Biol. Phys., vol. 71, pp. 1167-1174 (2008).

M.J. Williams et al., "Multicentre Quality Assurance of Intensity-Modulated Radiation Therapy Plans: A Precursor to Clinical Trials," Australas Radiol., vol. 51, pp. 472-479 (2007).

A.S. Reese et al., "Integral Dose Conservation in Radiotherapy," Med. Phys., vol. 36, pp. 731-740 (2009).

E. Astreinidou et al., "Level II Lymph Nodes and Radiation-Induced Xerostomia," Int. J. Radiat. Oncol. Biol. Phys., vol. 58, pp. 124-131 (2004).

B.V. Asselen et al., "The Dose to the Parotid Glands with IMRT for Oropharyngeal Tumors: The Effect of Reduction of Positioning Margins," Radiother Oncol., vol. 64, pp. 197-204 (2002).

K.A. Vineberg et al., "Is Uniform Target Dose Possible in IMRT Plans in the Head and Neck," Int. Radiat. Oncol. Biol. Phys., vol. 52, pp. 1159-1172 (2002).

M.A. Hunt et al., "Geometric Factors Influencing Dosimetric Sparing of the Parotid Glands Using IMRT," Int. J. Radiat. Oncol. Biol. Phys., vol. 66, pp. 296-304 (2006).

T. Saito et al., "New Algorithms for Euclidean Distance Transformation of an n-Dimensional Digitized Picture with Applications," Pattern Recognition, vol. 27, pp. 1551-1565 (1994).

E.B. Bulter et al., "Smart (Simultaneous Modulated Accelerated Radiation Therapy) Boost: A New Accelerated Fractionation Schedule for the Treatment of Head and Neck Cancer with intensity Modulated Radiotherapy," Int. J. Radiat. Oncol. Biol. Phys., vol. 45, pp. 21-32 (1999).

A. Eisbruch et al., Phase Study of Conformal and Intensity Modulated Irradiation for Propharyngeal Cancer. (Radiation therapy oncology group 0022, 2004).

L.B. Harrison et al., "Detailed Quality of Life Assessment in Patients Treated with Primary Radiotherapy for Cancer of the Base of Tongue," Head & Neck, vol. 19, pp. 169-175 (1997).

K. Bjordal et al., "Quality of Life in Patients Treated for Head and Neck Cancer: A Follow-Up Study 7 to 11 Years After Radiotherapy," Int. J. Radiat. Oncol. Biol. Phys., vol. 28, pp. 847-856 (1994).

Michael Kazhdan et al., "A Shape Relationship Descriptor for Radiation Therapy Planning", Medical Image Computing and Computer-Assisted Intervention (MICCAI 2009), LNCS 5762, Part II, pp. 100-108, Jan. 1, 2009.

U.S. Appl. No. 12/690,471.

Tremoleda et al., Imaging technologies for preclinical models of bone and joint disorders, EJNMMI Research 2011, 1:11.

Hindorf et al., EANN Dosimetry Committee guidelines for bone and whole-body dosimetry, Eur J Nucl Med Mol Imaging, Published online: Apr. 22, 2010.

Hong Song et al., "213Bi ($\alpha$-Emitter)—Antibody Targeting of Breast Cancer Metastases in the neu-N Transgenic Mouse Model", Cancer Res, vol. 68, No. 10, pp. 3873-3880, May 15, 2008.

Abstract of V.J. Lewinton et al., "Alpharadin, a Novel, Targeted Approach for Treatment of Bone Metastases from CRPC-Calculated Alpha-Particle Dosimetry Compared to a Favorable Clinical Safety Profile", ASCO Genitourinary Cancers Symposium, San Francisco, CA, USA (2 pages) (2010).

V.J. Lewinton et al., "Alpharadin, a Novel, Targeted Approach for Treatment of Bone Metastases from CRPC-Calculated Alpha-Particle Dosimetry Compared to a Favorable Clinical Safety Profile", ASCO Genitourinary Cancers Symposium, San Francisco, CA, USA (1 page) (2010).

George Sgouros et al., "Pharmacokinetics and dosimetry of an alpha-particle emitter labeled antibody: 213Bi-HuM195 (anti-CD33) in patients with leukemia", The Journal of Nuclear Medicine, vol. 40, No. 11, pp. 1935-1946, Nov. 1999.

(56) References Cited

OTHER PUBLICATIONS

M. Cristy et al., "ORNL/TM-8381/V1: Specific Absorbed Fractions of Energy at Various Ages for Internal Photon Sources", Oak Ridge National Laboratory, Apr. 1987 (100 pages).
J. Schwartz et al., "Renal Uptake of Bismuth-213 and its Contribution to Kidney Radiation Dose Following Administration of Actinium-225-Labeled Antibody", Physics in Medicine Biology, vol. 56, pp. 721-733, Feb. 7, 2011.
Robert F. Hobbs et al. "A Model of Cellular Dosimetry for Macroscopic Tumors in Radiopharmaceutical Therapy", Med. Phys., vol. 38, No. 6, pp. 2892-2903, Jun. 2011.
Dinyar B. Bhathena, "Glomerular Size and the Association of Focal Glomerulosclerosis in Long-Surviving Human Renal Allografts", Journal of the American Society of Nephrology, vol. 4, No. 6, pp. 1316-1326, Dec. 1993.
Loevinger R, Budinger TF, Watson EE. MIRD Primer for Absorbed Dose Calculations. New York, NY, USA: The Society of Nuclear Medicine, Inc.; 1991 (141 Pages).
Thomas M. Behr et al., "Correlation of Red Marrow Radiation Dosimetry with Myelotoxicity: Empirical Factors Influencing the Radiation-Induced Myelotoxicity of Radiolabeled Antibodies, Fragments and Peptides in Pre-Clinical and Clinical Settings", Cancer Biotherapy and Radiopharmaceuticals, vol. 17, No. 4, pp. 445-464, Aug. 2002.
Jostein Dahle et al. "Relative Biologic Effects of Low-Dose-Rate Alpha-Emitting 227Th-Rituximab and Beta-Emitting 90Y-Tiuexetan-lbritumomab Versus External Beam X-Radiation", Int. J. Radiation Oncology Biol. Phys., vol. 72, No. 1, pp. 186-192, Sep. 2008.
W.S. Snyder et al., ""S" Absorbed Dose per Unit Cumulated Activity for Selected Radionuclides and Organs", MIRD Pamphlet No. 11, New York, NY, USA: Society of Nuclear Medicine; Oct. 1975 (69 pages).
Wesley E. Bolch et al., "MIRD Pamphlet No. 17: The Dosimetry of Nonuniform Activity Distributions—Radionuclide S Values at the Voxel Level", The Journal of Nuclear Medicine, vol. 40, No. 1, pp. 11S-36S, Jan. 1999.
Michael G. Stabin et al. "OLINDA/EXM: The Second-Generation Personal Computer Software for Internal Dose Assessment in Nuclear Medicine", The Journal of Nuclear Medicine, vol. 46, No. 6, pp. 1023-1027, Jun. 2005.
George Sgouros et al., "MIRD Pamphlet No. 22 (abridged): Radiobiology and Dosimetry of Alpha-Particle Emitters for Targeted Radionuclide Therapy", The Journal of Nuclear Medicine, vol. 51, No. 2, pp. 311-328, Feb. 2010.
Michael R. McDevitt et al., "Radioimmunotherapy with Alpha-Emitting Nuclides", European Journal of Nuclear Medicine, vol. 25, No. 9, pp. 1341-1351, Sep. 1998.
Gamal Akabani et al., "Microdosimetric Analysis of Alpha-Particle-Emitting Targeted Radiotherapeutics Using Histological Images", The Journal of Nuclear Medicine, vol. 44, No. 5, pp. 792-805, May 2003.
Gamal Akabani et al., "Microdosimetry of Astatine-211 Using Histological Images: Application to Bone Marrow", Radiation Research, vol. 148, pp. 599-607 (1997).
E. Aurlien et al., "Exposure of Human Osteosarcoma and Bone Marrow Cells to Tumour-Targeted Alpha-Particles and Gamma-Irradiation: Analysis of Cell Survival and Microdosimetry", Int J Radiat Biol., vol. 76, No. 8, pp. 1129-1141 (2000).
Gjermund Henriksen et al., "Targeting of Osseous Sites with Alpha-Emitting 223Ra: Comparison with the Beta-Emitter 89Sr in Mice", The Journal of Nuclear Medicine, vol. 44, No. 2, pp. 252-259, Feb. 2003.
Seyed K. Imam, "Advancements in Cancer Therapy with Alpha-Emitters: a Review", Int. J. Radiation Oncology Biol. Phys., vol. 51, No. 1, pp. 271-278 (2001).
Ase M. Ballangrud et al., "Response of LNCaP Spheroids After Treatment with an Alpha-Particle Emitter (213Bi)-Labeled Anti-Prostate-Specific Membrane Antigen Antibody (J591)1", Cancer Research, vol. 61, pp. 2008-2014, Mar. 1, 2001.
G.W. Barendsen et al., "Irradiation of Human Cells in Tissue Culture with Alpha-Rays, Beta-Rays and X-Rays", International Journal of Radiation Biology and Related Studies in Physics Chemistry and Medicine, vol. 2, No. 4, pp. 441-443, Oct. 1960.
J. L. Humm, "A Microdosimetric Model of Astatine-211 Labeled Antibodies for Radioimmunotherapy", Int J Radiation Oncology Biol. Phys., vol. 13, No. 11, pp. 1767-1773, Nov. 1987.
Michael R. McDevitt et al., "Tumor Therapy with Targeted Atomic Nanogenerators", Science, vol. 294, pp. 1537-1540, Nov. 16, 2001.
Jaspreet Singh Jaggi et al., "Efforts to Control the Errant Products of a Targeted in Vivo Generator", Cancer Research, vol. 64, No. 11, pp. 4888-4895, Jun. 1, 2005.
George Sgouros, "Long-Lived Alpha Emitters in Radioimmunotherapy: The Mischievous Progeny", Cancer Biotherapy Radiopharmaceuticals, vol. 15, No. 3, pp. 219-221 (2000).
Michael R. Zalutsky et al., "Targeted Alpha-Particle Radiotherapy with 211 At-Labeled Monoclonal Antibodies", Nuclear Medicine and Biology, vol. 34, pp. 779-785 (2007).
Michael R. Zalutsky et al., "Radioimmunotherapy with Alpha-Particle Emitting Radioimmunoconjugates", Acta Oncologica, vol. 35, No. 3, pp. 373-379 (1996).
Michael R. McDevitt et al., "An Alpha-Particle Emitting Antibody ([213Bi]J591) for Radioimmunotherapy of Prostate Cancer", Cancer Research, vol. 60, pp. 6095-6100, Nov. 1, 2000.
Gjermund Henriksen et al., "Significant Antitumor Effect from Bone-Seeking, Alpha-Particle-Emitting (223)Ra Demonstrated in an Experimental Skeletal Metastases Model", Cancer Research, vol. 62, pp. 3120-3125, Jun. 1, 2002.
L. Arazi et al., "The Treatment of Solid Tumors by Alpha Emitters Released from (224)Ra-Loaded Sources-Internal Dosimetry Analysis", Physics in Medicine and Biology, vol. 55, pp. 1203-1218 (2010).
Hakan Andersson et al., "Intraperitoneal Alpha-Particle Radioimmunotherapy of Ovarian Cancer Patients: Pharmacokinetics and Dosimetry of (211)At-MX35 F(ab')2—A Phase I Study", The Journal of Nuclear Medicine, vol. 50, No. 7, pp. 1153-1160, Jul. 2009.
Abstract of M. R. Zalutsky et al., "Radioimmunotherapy of Recurrent Glioma Patients Using Alpha-Particle Emitting Astatine-211 Labeled Chimeric Anti-Tenascin Monoclonal Antibody", The 48th SNM Annual Meeting, A Supplement to The Journal of Nuclear Medicine, vol. 42, No. 5, pp. 121P-122P, May 2001, Supplement.
Michael R. Zalutsky et al., "Clinical Experience with Alpha-Particle Emitting 211At-Labeled Chimeric Antitenascin Monoclonal Antibody 81C6", The Journal of Nuclear Medicin, vol. 49, No. 1, pp. 30-38, Jan. 2008.
Joseph G. Jurcic et al., al. Targeted Alpha Particle Immunotherapy for Myeloid Leukemia, Blood, vol. 100, No. 4, pp. 1233-1239, Aug. 15, 2002.
Abstract of J.G. Jurcic et al., "Alpha-Particle Immunotherapy for Acute Myeloid Leukemia (AML) with Bismuth-213 and Actinium-225", Cancer Biother Radiopharm., vol. 21, No. 4, pp. 396, Sep. 25, 2006.
Stefan Kneifel et al., "Local Targeting of Malignant Gliomas by the Diffusible Peptidic Vector 1,4,7,10-Tetraazacyclododecane-1-Glutaric Acid-4,7,10-Triacetic Acid-Substance P", Clin. Cancer Res., vol. 12, No. 12, pp. 3843-3850, Jun. 15, 2006.
Knut Liepe, "Alpharadin, a 223Ra-Based Alpha-Particle-Emitting Pharmaceutical for the Treatment of Bone Metastases in Patients with Cancer", Current Opinion in Investigational Drugs, vol. 10, No. 12, pp. 1346-1358 (2009).
Oyvind S. Bruland et al., "High-Linear Energy Transfer Irradiation Targeted to Skeletal Metastases by the Alpha-Emitter 223Ra: Adjuvant or Alternative to Conventional Modalities?", Clin. Cancer Res., vol. 12, No. 20 Suppl, pp. 6250s-6257s, Oct. 15, 2006.
E. Menapace et al., "Comparison Between Theoretical Calculation and Experimental Results of Excitation Functions for Production of Relevant Biomedical Radionuclides", .CP769, International Conference on Nuclear Data for Science and Technolgoy, pp. 1638-1641 (2005).
T.R. Butz et al., "233U Disposition Medical Isotope Production and Building 3019 Complex Shutdown Project", 2005 NCSD Topical Meeting: Integrating Criticality Safety into the Resurgence of Nuclear Power, American Nuclear Society, Sep. 19-22, 2005 (14 pages).

(56) References Cited

OTHER PUBLICATIONS

Martin W. Brechbiel, "Targeted Alpha Therapy: Past, Present, future?", Dalton Transactions, pp. 4918-4928 (2007).
L.I. Guseva et al., "Development of a Tandem Generator System 229Th/225Ac/213Bi for Repeated Production of Short-Llived Alpha-Emitting Radionuclides", Radiochemistry, vol. 51, No. 2, pp. 169-174, (2009).
Fred Ramsey et al., "Converting an AEG Cyclotron to H-Acceleration and Extraction", CP1009, Application of Acelerators in Research and Industry: 20th International Conference, pp. 500-503 (2009).
L.I. Guseva et al., "A Ggenerator System for Production of Medical Alpha-Radionuclides Ac-225 and Bi-213", Journal of Radioanalytical and Nuclear Chemistry, vol. 285, pp. 667-673 ( 2010).
Abstract of R. Hultborn et al. "Pharmacokinetics and Dosimetry of (211)AT-MX35 F(AB')2 in Therapy of Ovarian Cancer—Preliminary Results from an Ongoing Phase I Study", Cancer Biotherapy and Radiopharmaceuticals, vol. 21, No. 4, pp. 395, Sep. 25, 2006.
Abstract of S. Nilsson et al., "Clinical Experience and Radiation Safety of the First-in-Class Alpha-Pharmaceutical, Alpharadin (Radium-223) in Patients with Castration-Resistant Prostate Cancer (CRPC) and Bone Metastases", International Journal of Radiation Oncology Biology Physics, vol. 78, No. 3 Supplemental pp. S375-S376 (2010).
Sandra J. Horning et al., "Efficacy and Safety of Tositumomab and Iodine-131 Tositumomab (Bexxar) in B-Cell Lymphoma, Progressive After Rituximab", Journal of Clinical Oncology, vol. 23, No. 4, pp. 712-719, Feb. 1, 2005.
Thomas E. Witzig et al., "Safety of Yttrium-90 Ibritumomab Tiuxetan Radioimmunotherapy for Relapsed Low-Grade, Follicular, or Transformed Non-Hodgkin's Lymphoma", Journal of Clinical Oncology, vol. 21, No. 7, pp. 1263-1270, Apr. 1, 2003.
George Sgouros, "Bone Marrow Dosimetry for Radioimmunotherapy: Theoretical Considerations", The Jouranl of Nuclear Medicine, vol. 34, No. 4, pp. 689-694, Apr. 1993.
Christopher J. Watchman et al., "Absorbed Fractions for Alpha-Particles in Tissues of Cortical Bone", Phys. Med. Biol., vol. 54, pp. 6009-6027, Sep. 22, 2009.
Christopher J. Watchman et al., "Spatial Distribution of Blood Vessels and CD34+ Hematopoietic Stem and Progenitor Cells Within the Marrow Cavities of Human Cancellous Bone", The Journal of Nuclear Medicine, vol. 48, No. 4, pp. 645-654, Apr. 2007.
Christopher J. Watchman et al., "Absorbed Fractions for Alpha-Particles in Tissues of Trabecular Bone: Considerations of Marrow Cellularity Within the ICRP Reference Male", The Journal of Nuclear Medicine, vol. 46, No. 7, pp. 1171-1185, Jul. 2005.
James M. Brindle et al., "Correlations of Total Pelvic Spongiosa Volume with Both Anthropometric Parameters and Computed Tomography-Based Skeletal Size Measurements", Cancer Biotherapy and Radiopharmaceuticals, vol. 21, No. 4, pp. 352-363 (2006).
James M. Brindle et al., "CT Volumetry of the Skeletal Tissues", Med. Phys., vol. 33, No. 10, pp. 3796-3803, Oct. 2006.
James M. Brindle et al., "Linear Regression Model for Predicting Patient-Specific Total Skeletal Spongiosa Volume for Use in Molecular Radiotherapy Dosimetry", The Journal of Muclear Medicine, vol. 47, No. 11, pp. 1875-1883, Nov. 2006.
W.E. Botch et al., "Skeletal Absorbed Fractions for Electrons in the Adult Male: Considerations of a Revised 50-Microm Definition of the Bone Endosteum", Radiation Protection Dosimetry, vol. 127, No. 1-4, pp. 169-173, Jun. 7, 2007.
Vincent A. Bourke et al., "Spatial Gradients of Blood Vessels and Hematopoietic Stem and Progenitor Cells Within the Marrow Cavities of the Human Skeleton", Blood, vol. 114, No. 19, pp. 4077-4080, Nov. 5, 2009.
J.G. Hunt et al., "Calculation of Absorbed Fractions to Human Skeletal Tissues Due to Alpha Particles Using the Monte Carlo and 3-D Chord Based Transport Techniques", Radiation Protection Dosimetry, vol. 127, No. (1-4), pp. 223-226, Jun. 14, 2007.
Choonik Lee et al., "An Assessment of Bone Marrow and Bone Endosteum Dosimetry Methods for Photon Sources", Phys. Med. Biol., vol. 51, pp. 5391-5407, Oct. 6, 2006.
Jose C. Pichardo et al., "Method for Estimating Skeletal Spongiosa Volume and Active Marrow Mass in the Adult Male and Adult Female", The Journal of Nuclear Medicine, vol. 48, No. 11, pp. 1880-1888, Nov. 2007.
D.A. Rajon et al., "Image Segmentation of Trabecular Spongiosa by Visual Inspection of the Gradient Magnitude", Phys. Med. Biol., vol. 51, pp. 4447-4467, Aug. 22, 2006.
Dik J. Kwekkeboom et al., "Overview of Results of Peptide Receptor Radionuclide Therapy with 3 Radiolabeled Somatostatin Analogs", The Journal of Nuclear Medicine, vol. 46, No. 1 (Suppl), pp. 62S-66S, Jan. 2005.
Jean Claude Reubi et al., "Affinity Profiles for Human Somatostatin Receptor Subtypes SST1-SST5 of Somatostatin Radiotracers Selected for Scintigraphic and Radiotherapeutic use", European Jouranl of Nuclear Medicine, vol. 27, No. 3, pp. 273-282, Mar. 2000.
Lionel G. Bouchet et al., "MIRD Pamphlet No. 19: Absorbed Fractions and Radionuclide S Values for Six Age-Dependent Multiregion Models of the Kidney", The Journal of Nuclear Medicine, vol. 44, No. 7, pp. 1113-1147, Jul. 2003.
Hong Song et al., "Radioimmunotherapy of Breast Cancer Metastases with Alpha-Particle Emitter 225Ac: Comparing Efficacy with 213Bi and 90Y", Cancer Res., vol. 69, No. 23, pp. 8941-8948, Dec. 1, 2009.
Jaspreet Singh Jaggi et al., "Renal Tubulointerstitial Changes After Internal Irradiation with Alpha-Particle-Emitting Actinium Daughters", J. Am. Soc. Nephrol., vol. 16, pp. 2677-2689 (2005).
Jaspreet Singh Jaggi et al., "Mitigation of Radiation Nephropathy After Internal Alpha-Particle Irradiation of Kidneys", Int. J. Radiat. Oncol. Biol. Phys., vol. 64, No. 5, pp. 1503-1512 (2006).
Tom Back et al., "Glomerular Filtration Rate After Alpha-Radioimmunotherapy with 211At-MX35-F(ab')2: a Long-Term Study of Renal Function in Nude Mice", Cancer Biotherapy Radiopharmaceuticals, vol. 24, No. 6, pp. 649-658 (2009).
S. Agostinelli et al., GEANT4—A Simulation Toolkit, Nuclear Instruments and Methods in Physcis Research A, vol. 506, pp. 250-303 (2003).
M. Pacilio et al., "Differences Among Monte Carlo Codes in the Calculations of Voxel S Values for Radionuclide Targeted Therapy and Analysis of Their Impact on Absorbed Dose Evaluations", Med. Phys., vol. 35, No. 5, pp. 1543-1552, May 2009.
N. Chouin et al., "Evidence of Extranuclear Cell Sensitivity to Alpha-Particle Radiation Using a Microdosimetric Model. I. Presentation and Validation of a Microdosimetric Model", Radiation Research, vol. 171, pp. 657-663 (2009).
N. Chouin et al., "Evidence of Extranuclear Cell Sensitivity to Alpha-Particle Radiation Using a Microdosimetric Model. II. Application of the Microdosimetric Mmodel to Experimental Results", Radiation Research, vol. 171, pp. 664-673 (2009).
Robert Hobbs, "A Trabecular Model of Bone Marrow Toxicity for 223Ra Alpha-Emitter Radiopharmaceutical Therapy", The Journal of Nuclear Medicine, vol. 52 (Supplemental 1), pp. 130 (2011).
Amish P. Shah et al., "Adipocyte Spatial Distributions in Bone Marrow: Implications for Skeletal Dosimetry Models", The Journal of Nuclear Medicine, vol. 44, No. 5, pp. 774-783, May 2003.
Amish P. Shah et al., "A Paired-Image Radiation Transport Model for Skeletal Dosimetry", The Journal of Nuclear Medicine, vol. 46, No. 2, pp. 344-353, Feb. 2005.
Matthew Hough et al., "An Image-Based Skeletal Dosimetry Model for the ICRP Reference Adult Male-Iinternal Electron Sources", Phys. Med. Biol., vol. 56, pp. 2309-2346 (2011).
Perry B. Johnson et al., "Response Functions for Computing Absorbed Dose to Skeletal Tissues from Photon Irradiation—An Update", Phys. Med. Biol., vol. 56, pp. 2347-2365 (2011).
Sebastien Baechler et al., "Predicting Hematologic Toxicity in Patients Undergoing Radioimmunotherapy with 90Y-Ibritumomab Tiuxetan or 131I-Tositumomab", The Journal of Nuclear Medicine, vol. 51, No. 12, pp. 1878-1884, Dec. 2010.
Tom Back et al., "The Alpha-Camera: A Quantitative Digital Autoradiography Technique Using a Charge-Coupled Device for Ex

(56) References Cited

OTHER PUBLICATIONS

Vivo High Resolution Bioimaging of Alpha-Particles", The Journal of Nuclear Medicine, vol. 51, No. 10, pp. 1616-1623, Oct. 2010.
Sui Shen et al., "A Preliminary Cell Kinetics Model of Thrombocytopenia After Radioimmunotherapy", The Journal of Nuclear Medicine, vol. 39, No. 7, pp. 12231229, Jul. 1998.
GaryL. Rosner et al., "Pharmacodynamic Analysis of Hematologic Profiles", Journal of Pharmacokinetics and Biopharmaceutics, vol. 22, No. 6, pp. 499-524 (1994).
Abstract of S. Baechler et al., "A Kinetic Model of Patient Platelets After Radioimmunotherapy", 55th SNM Annual Meeting, Abstract Book Supplement to The Journal of Nuclear Medicine, vol. 49, Supplement 1, pp. 48P, May 2008.
H. Song et al., "An Immunotolerant HER-2/neu Transgenic Mouse Model of Metastatic Breast Cancer", Clin. Cancer Res., vol. 14, N. 19, p. 6116-6124, Oct. 1, 2008.
U.S. Appl. No. 12/514,853, 2010-0061607, Sgouros, et al., Mar. 11, 2010.
U.S. Appl. No. 12/687,670, 2011-0135058, Sgouros, et al., Jun. 9, 2011, U.S. Pat. No. 8,693,629.
U.S. Appl. No. 12/690,471, 2011-0176018, Sgouros, et al., Jul. 21, 2011, U.S. Pat. No. 8,914,237.
U.S. Appl. No. 12/820,852, 2011-0153547, McNutt, et al., Jun. 23, 2011, U.S. Pat. No. 8,688,618.
U.S. Appl. No. 13/335,565, 2013-0165732, Sgouros, et al., Jun. 27, 2013.
U.S. Appl. No. 14/170,020, 2014-0149335, McNutt, et al., May 29, 2014.
PCT/US2013/072147, Nov. 27, 2013.
U.S. Appl. No. 14/438,132, 2015-0286796, Hobbs, et al., Oct. 8, 2015.
U.S. Appl. No. 14/438,132.
International Search Report issued in International Application No. PCT/US2013/066872 dated Apr. 24, 2014.
Written Opinion issued in International Application No. PCT/US2013/066872 dated Apr. 24, 2014.
George Sgouros et al., "3-D Imaging Based, Radio Biological Dosimetry", Semin. Nucl. Med. vol. 38, No. 5, pp. 321-334, Sep. 2008.
Stephen K. Gerard et al., "131I Dosimetry and Thyroid Stunning", The Journal of Nuclear Medicine, vol. 44, No. 12, pp. 2039-2040, Dec. 2003.
Ernest L. Mazzaferri et al., "Clinical Review 128: Current Approaches to Primary Therapy for Papillary and Follicular Thyroid Cancer", The Journal of Clinical Endocrinology and Metabolism, vol. 88, No. 6, pp. 1447-1463 (2001).
Fabrice Le Gall et al., "Di-, Tri-, and Tetrameric Single Chain Fv Antibody Fragmetns Against Human CD19: Effect of Valency on Cell Binding", FEBS Letters, vol. 453, pp. 164-168 (1999).
Isabelle Clairand et al., "Dose3d: EGS4 Monte Carlo Code-Based Software for Internal Radionuclide Dosimetry", Journal of Nuclear Medicine, vol. 40, No. 9, pp. 1517-1523, Sep. 1999.
George Sgouros, "Dosimetry of Internal Emitters", The Journal of Nuclear Medicine, vol. 46, No. 1 (Suppl), pp. 18S-27S, Jan. 2005.
Robert Dorn et al., "Dosimetry-Guided Radioactive Iodine Treatment in Patients with Metastatic Differentiated Thyroid Cancer: Largest Safe Dose Using a Risk-Adapted Approach, The Journal of Nuclear Medicine, vol. 44, No. 3, pp. 451-456, Mar. 2003.
Thomas M. Behr et al., "Experimetnal Studies on the Role of Antibody Fragments in Cancer Radio-immunotherapy: Influence of Radiation Dose and Dose Rate on Toxicity and Anti-Tumor Efficacy", Int. J. Cancer, vol. 77, pp. 787-795 (1998).
Katherine S. Kolbert et al., Implementation and Evaluation of Patient-Specific Three-Dimensional Internal Dosimetry, The Journal of Nuclear Medicine, vol. 38, No. 2. pp. 301-308 (Feb. 1997).
Heribert Hanscheid et al., "Iodine Biokinetics and Dosimetry in Radioiodiine Therapy of Thyroid Cancer: Procedures and Results of a Prospective International Controlled Study of Ablation After rhTSH or Hormone Withdrawal", The Journal of Nuclear Medicine, vol. 47, No. 4, pp. 648-654, Apr. 2006.
Andreas Otte et al., "Is Radiation Nephropathy Caused by yttrium-90?", The Lancet, vol. 359, pp. 979, Mar. 16, 2002.
Hong Song et al., "Lung Dosimetry for Radioiodine Treatment Planning in the Case of Diffuse Lung Metastases", The Journal of Nuclear Medicine, vol. 47, No. 12, pp. 1985-1994, Dec. 2006.
Sui Shen et al., "Model Prediction of Treatment Planning for Dose-Fractionated Radioimmunotherpary", Cancer, vol. 94, No. 4, pp. 1264-1269, Feb. 15, 2002.
J.L. Humm et al., "Nonuniformity of Turmo Dose in Radioimmunotherpary", The Journal of Nuclear Medicine, vol. 31, No. 1, pp. 75-83, Jan. 1990.
Lynne J. Lawrence et al., "Orientation of Antigen Binding Sites in Dimeric and Tirmeric Single Chain Fv Antibody Fragments", FEBS Letters, vol. 45, pp. 479-484 (1998).
George Sgouros et al., "Patient-Specific Dosimetry for 131I Thyroid Cancer Therapy Using 124I PET and 3-Dimensional-Internal Dosimetry (3D-ID) Software", The Journal of Nuclear Medicine, vol. 45, No. 8, pp. 1366-1372, Aug. 2004.
Aban Meyer Samuel et al., "Polmonary Metastases in Children and Adolescents with Well-Differentiated Thyroid Cancer", The Journal of Nuclear Medicine, vol. 39, No. 9, pp. 1531-1536, Sep. 1998.
Eric P. Cohen et al., "Radiation Nephropathy Caused by yttrium 90", The Lancet, vol. 358, pp. 1102-1103, Sep. 29, 2001.
Gerald L. DeNardo et al., "Rationales, Evidence, and Design Considerations for Fractionated Radioimmunotherapy", Cancer, vol. 94, No. 4, pp. 1332-1348, Feb. 15, 2002.
John L. Atwell et al., "scFv Multimers of the Anti-Neuraminidase Antibody NC10: Length of the Linker between VH and VL Domains Dictates Precisely the Transition Between Diabodies and Triabodies", Protein Engineering, vol. 12, No. 7, pp. 597-604 (1999).
Joseph A. O'Donoghue et al., "Single-Dose Versus Fractionated Radioimmunotherapy: Model Comparisons for Uniform Tumor Dosimetry", The Journal of Nuclear Medicine, vol. 41, No. 3, pp. 538-547, Mar. 2000.
Richard J. Robbins et al., "The Evolving Role of 131I for the Treatment of Differentiated Thyroid Carcinoma", The Journal of Nuclear Medicine, vol. 46, No. 1 (Suppl), pp. 28S-37S, Jan. 2005.
Glenn D. Flux et al., "Three-Dimensional Dosimetry for Intralesional Radionuclide Therapy Using Mathematical Modeling and Multimodality Imaging", The Journal of Nuclear Medicine, vol. 38, No. 7, pp. 1059-1066, Jul. 1997.
Peter L. Roberson et al., "Three-Dimensional Reconstrcution of Monoclonal Antibody Uptake in Tumore and Calculation of Beta Dos-Rate Nonuniformity", Cancer, vol. 73, No. 3 (Suppl), pp. 912-918, Feb. 1, 1994.
Dandamudi V. Rao et al., "Time-Dose-Fractionation in Radioimmunotherapy: Implications for Selecting Radionuclides", The Journal of Nuclear Medicine, vol. 34, No. 10, pp. 1801-1810, Oct. 1993.
George Sgouros et al., "Treatment Planning for Internal Radionuclide Therapy: Three-Dimensional Dosimetry for Nonuniformly Distributed Radionuclides", The Journal of Nuclear Medicine, vol. 31, No. 11, pp. 1884-1891, Nov. 1990.
Joseph G. Rajendran et al., "Tumor Hypoxia Imaging with [F-18] Fluoromisonidazole Positron Emission Tomography in Head and Neck Cancer", Clin. Cancer Res., vol. 12, No. 18, pp. 5435-5441, Sep. 15, 2006.
Hui Zhu et al., "Tumor Pretargeting for Radioimmunodetection and Radioimmunotherapy", The Journal of Nuclear Medicine, vol. 39, No. 1, pp. 65-76, Jan. 1998.
U.S. Appl. No. 13/335,565.
E.E. Furhang et al., "Implementation of a Monte Carlo Dosimetry Method for Patient-Specific Internal Emitter Therapy", Med. Phys., vol. 24, No. 7, pp. 1163-1172, Jul. 1997.
Michael Stabin, "Nuclear Medicine Dosimetry", Phys. Med. Biol., vol. 51, pp. R187-R202 (2006).
An Liu et al., "Monte Carlo-Assisted Voxel Source Kernal Method (MAVSK) for Internal Beta Dosimetry", Nuclear Medicine & Biology, vol. 25, pp. 423-433 (1998).
A.K. Erdi et al., "Use of the Fast Hartley Transform for Efficient 3D Convolution in Calculation of Radiation Dose", IEEE, pp. 639-640 (1994).

(56) References Cited

OTHER PUBLICATIONS

Matthew J. Guy et al., "RMDP: A Dedicated Package for 131I SPECT Quantification, Registration and Patient-Specific Dosimetry", Cancer Biotherapy & Radiopharmaceuticals, vol. 18, No. 1, pp. 61-69 (2003).
Marie-Anne Descalle et al., "Application of Minerva Monte Carlo Simulations to Targeted Radionuclide Therapy", Cancer Biotherapy & Radiopharmaceuticals, vol. 18, No. 1, pp. 71-79 (2003).
S, Chiavassa et al., "Validation of a Personalized Dosimetric Evaluation Tool (Oedipe) for Targeted Radiotherapy Based on the Monte Carlo MCNPX Code", Phys. Med. Biol., vol. 51, pp. 601-616 (2006).
Moorthy S. Muthuswamy et al., "A Quantitave Study of Radionuclide Characteristics for Radioimmunotherapy from 3D Reconstrucions Using Serial Autoradiography", Int. J. Radiation Oncology Biol. Phys., vol. 35, No. 1, pp. 165-172 (1996).
Aiden A. Flynn et al., "Optimizing Radioimmunotherapy by Matching Dose Distributinon with Tumor Structure Using 3D Reconstructions of Serial Images", Cancer Biotherapy & Radiopharmaceuticals, vol. 16, No. 5, pp. 391-400 (2001).
Roger W. Howell et al., "Macroscopic Dosimetry for Radioimmunotherapy: Nonuniform Activity Districutions in Solid Tumors", Med. Phys., vol. 16, No. 1, pp. 66-74, Jan.-Feb. 1989.
Aiden A. Flynn et al., "The Nonuniformity of Antibody Distribution in the Kidney and its Influence on Dosimetry", Radiation Research, vol. 159, pp. 182-189 (2003).
Eric J. Hall et al., "Radiation Dose-Rate: A Factor of Importance in Radiobiology and Radiotherapy", The British Journal of Radiology, vol. 45, No. 530, pp. 81-97, Feb. 1972.
G.W. Barendsen et al., "Dose Fractionation, Dose Rate and ISO-Effect Relationships for Normal Tissue Responses", Int. J. Radiation Oncology Bio. Phy., vol. 8, No. 11, pp. 1981-1997, Nov. 1982.
Rulon Mayer et al., "Direct Measurement of Intratumor Dose-Rate Distributions in Experimental Xenografts Treated with 90Y-Labeled Radioimmunotherapy", Int. J. Radiation Oncology Biol. Phys., vol. 32, No. 1, pp. 147-157 (1995).
Gamal Akabani et al., "Dosimetry and Dose-Response Relationships in Newly Diagnosed Patients with Malignant Gliomas Treated with Iodine-131-Labeled Anti-Tenascin Monoclonal Antibody 81C6 Therapy", Int. J. Radiation oncology Biol. Phys., vol. 46, No. 4, pp. 947-958 (2000).
A.A. Flynn et al., "Effectiveness of Radiolabelled Antibodies for Radio-Immunotherapy in a Colorectal Xenograft Model: A comparative Study Using the Linear-Quadratic Formulation", International Journal of Radiation Biology, vol. 77, No. 4, pp. 507-517 (2001).
Abstract of K.S. Kolert et al., "Display and Manipulation of SPECT and CT Studies for Radiolabeled Antibody Therapy", Cancer Biother Radiopharm, vol. 13, pp. 302 (1998).
Eli E. Furhang et al., "A Monte Carlo Approach to Patient-Specific Dosimetry", Med. Phys., vol. 23, No. 9, pp. 1523-1529, Sep. 1996.
J. Van Dyke et al., "Determination of Parameters for the Linear-Quadratic Model for Radiation-Induced Lung Damage", Int. J. Radiation oncology Biol. Phys., vol. 17, pp. 695 (1989).
Anthony Gaussen et al., "Radiosensitivity of Human Normal and Tumoral Thyroid Cells Using Fluoscence in situ Hybridization and Clonogenic Survival Assay", Int. J. Radiation oncology Biol. Phys., vol. 44, No. 33, pp. 683-691 (1999).
Cecile Challeton et al., "Characterization and Radiosensitivity at High or Low Dose Rate of Four Cell Lines Derived from Human Thyroid Tumors", Int. J. Radiation Oncology Biol. Phys., vol. 37, No. 1, pp. 163-169 (1997).
Eric C. Frey et al., "Application of Task-Based Measures of Image Quality to Optimization and Evaluation of Three-Dimensional Reconstruction-Based Compensation Methods in Myocardial Perfusion Spect", IEEE Transactions on Medical Imaging, vol. 21, No. 9, pp. 1040-1050, Sep. 2002.
David L. North et al., "Effective Half-Life of 131I in Thyroid Cancer Patients", Health Physics, vol. 81, No. 3, pp. 325-329, Sep. 2001.
Jen-Der Lin et al., "Papillary Thyroid Carcinomas with Lung Metastases", Thyroid, vol. 14, No. 12, pp. 1091-1096 (2004).
Johnathan R. Clark et al., "Variable Predicting Distant Metastases in Thyroid Cancer", The Laryngoscope, vol. 115, pp. 661-667, Apr. 2005.
C.M.L. West et al., "The Potential of PET to Increase Understanding of the Biological Basis of Tumour and Normal Tissue Respnose to Radiotherapy", The British Institute Of Radiology, PET Scanning in Radiotherpay, Supplement 28, pp. 50-54 (2005).
Hazel Breitz et al., "Dosimetry of High Dose Skeletal Targeted Radiotherapy (STR) with 166Ho-DOTMP", Cancer Biotherapy & Radiopharmaceuticals, vol. 18, No. 2, pp. 225-230 (2003).
Markus Cybulla et al., "End-Stage Renal Disease After Treatment with 90Y-DOTATOC", European Journal of Nuclear Medicine, vol. 28, No. 10, pp. 1552-1554, Oct. 2001.
David M. Goldenberg et al., "Antibody Pretargeting Advances Cancer Radioimmunodetection and Radioimmunotherapy", Journal of Clinical Oncology, vol. 24, No. 5, pp. 823-834, Feb. 10, 2006.
M. De Jong et al., "Therapy of Neuroendocrine Tumors with Radiolabeled Somatostatin-Analogues", The Quarterly Journal of Nuclear Medicine, vol. 43, No. 4, pp. 356-366, Dec. 1999.
Marion De Jong et al., "Somatostatin Receptor—Targeted Radionuclide Therapy of Tumors: Preclinical and Clinical Findings", Seminars in Nuclear Medicine, vol. 32, No. 2, pp. 133-140, Apr. 2002.
Magnus Tagesson et al., "A Monte-Carlo Program Converting Activity Distributions to Absorbed Dose Distributions in a Radionuclide Treatment Planning System", Acta Oncologica, vol. 35, No. 3, pp. 367-372 (1996).
H. Zaidi et al., "Therapeutic Applications of Monte Carlo Calculations in Nuclear Medicine", Philadelphi: Institus of Physics (2002) (345 pages).
J.E. Rail et al., "Radiation Pneumonitis and Firbrosis: A Complication of Radioiodine Treatment of Pulmonary Metastases from Cancer of the Thyroid", The Journal of Clinical Endocrinology and Metabolism, vol. 17, No. 11, pp. 1263-1276, Nov. 1957.
Alev K. Erdi et al., "Use of the Fast Hartley Transform for Three-Dimensional Dose Calculation in Radionuclide Therapy", Med. Phys., vol. 25, No. 11, pp. 2226-2233, Nov. 1998.
Timothy K. Johnson et al., "MABDOSE. I: Characterization of a General Purpose Dose Estimation Code", Med. Phys, vol. 26, No. 7, pp. 1389-1395, Jul. 1999.
A.A. Flynn et al., "Antibody and Radionuclide Characteristics and the Enhancement of the Effectiveness of Radioimmunotherapy by Selective Dose Delivery to Radiosensitive Areas of Tumour", International Journal of Radiation Biology, vol. 78, No. 5, pp. 407-415 (2002).
Abstract of K.S. Kolbert et al., "Dose-Volume Historgram Representation of Patient Dose Distribution in Three-Dimensional Internal Dosimetry", The Journal of Nuclear Medicine, vol. 35, No. 5, pp. 123P-124P, May 1994.
Richard S. Benua et al., "A Method and rationale For Treating Metastatic Thyroid Carcinoma with the Largest Safe Dose of 131I", Frontiers in Thryoidology, vol. 2, Plenum Medical Book Company, pp. 1317-1321, Sep. Jan. 6, 1985.
U.S. Appl. No. 14/170,020.

* cited by examiner

105

ASSUME ACTIVITY RETENTION LIMIT

110

USE ACTIVITY RETENTION LIMIT TO DETERMINE DOSE RATE FOR PHANTOM

115

USE DOSE RATE FOR PHANTOM TO DETERMINE DOSE RATE FOR OTHER PHANTOMS

120

USE DOSE RATE FOR OTHER PHANTOMS TO FIND ADMINISTERED ACTIVITY

125

OBTAIN MEAN ABSORBED DOSE

FIGURE 1

FIGURE 2 - Anatomic models

Real Patients

Real Patients

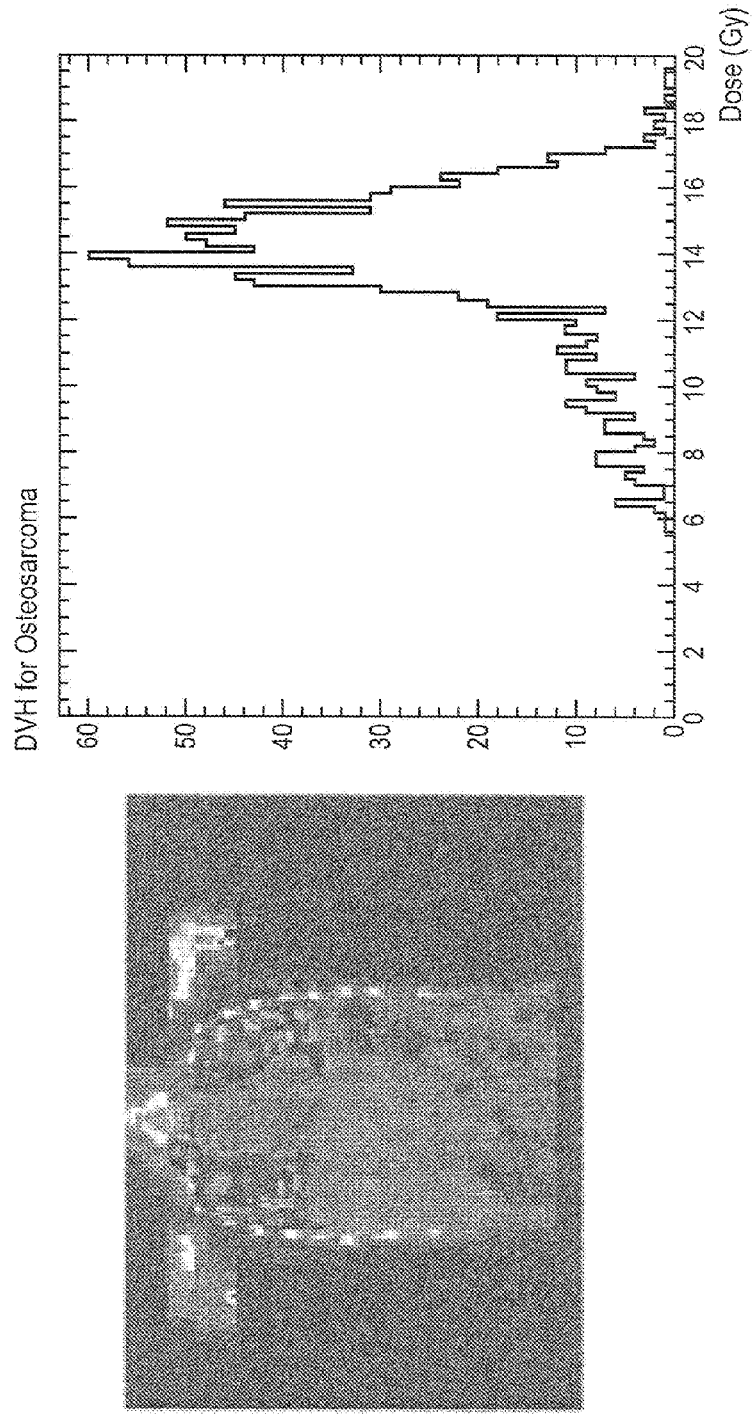
FIGURE 5 - Dose Map

| Reference Phantom | $M_{TB}$ (kg) | $M_{LU}$ (kg) | $S_{LU \leftarrow LU}$ (mGy/MBq-s) | $S_{LU \leftarrow TB}$ (mGy/MBq-s) | $S_{LU \leftarrow RB}$ (mGy/MBq-s) | $SP_{LU \leftarrow LU}$ (mGy/MBq-s) |
|---|---|---|---|---|---|---|
| Male adult | 73.7 | 1.00 | $3.40 \times 10^{-5}$ | $7.22 \times 10^{-7}$ | $1.92 \times 10^{-5}$ | $3.60 \times 10^{-6}$ |
| Female adult | 56.9 | 0.80 | $4.28 \times 10^{-5}$ | $9.34 \times 10^{-7}$ | $2.36 \times 10^{-5}$ | $4.80 \times 10^{-6}$ |
| 15-year-old | 56.8 | 0.65 | $5.16 \times 10^{-5}$ | $9.33 \times 10^{-7}$ | $2.98 \times 10^{-5}$ | $4.90 \times 10^{-6}$ |
| 10-year-old | 33.2 | 0.45 | $7.34 \times 10^{-5}$ | $1.48 \times 10^{-6}$ | $3.51 \times 10^{-5}$ | $6.29 \times 10^{-6}$ |

| $F_{48}$ | DRC (cGy/h) |
|---|---|
| 1.0 | 45.6 |
| 0.9 | 43.6 |
| 0.8 | 41.5 |
| 0.7 | 39.5 |
| 0.6 | 37.4 |

FIGURE 12

|  |  | $AA_{max}$ (GBq) | | $D_{LU}$ (Gy) | |
| --- | --- | --- | --- | --- | --- |
| Reference Phantom | $A_{TB}(t=48h)$ (GBq) | $T_{RB}=$ 20 h | $T_{RB}=$ 10 h | $T_{RB}=$ 20 h | $T_{RB}=$ 10 h |
| Male adult | 1.71 | 3.05 | 6.90 | 39.7 | 42.6 |
| Female adult | 1.36 | 2.42 | 5.49 | 39.7 | 42.6 |
| 15-year-old | 1.12 | 2.00 | 4.54 | 39.7 | 42.7 |
| 10-year-old | 0.80 | 1.42 | 3.23 | 39.8 | 42.3 |

FIGURE 16 – Radiobiological Modeling
- Equivalent Uniform Dose (EUD) is then
- Biologically Effective Dose (BED) is then
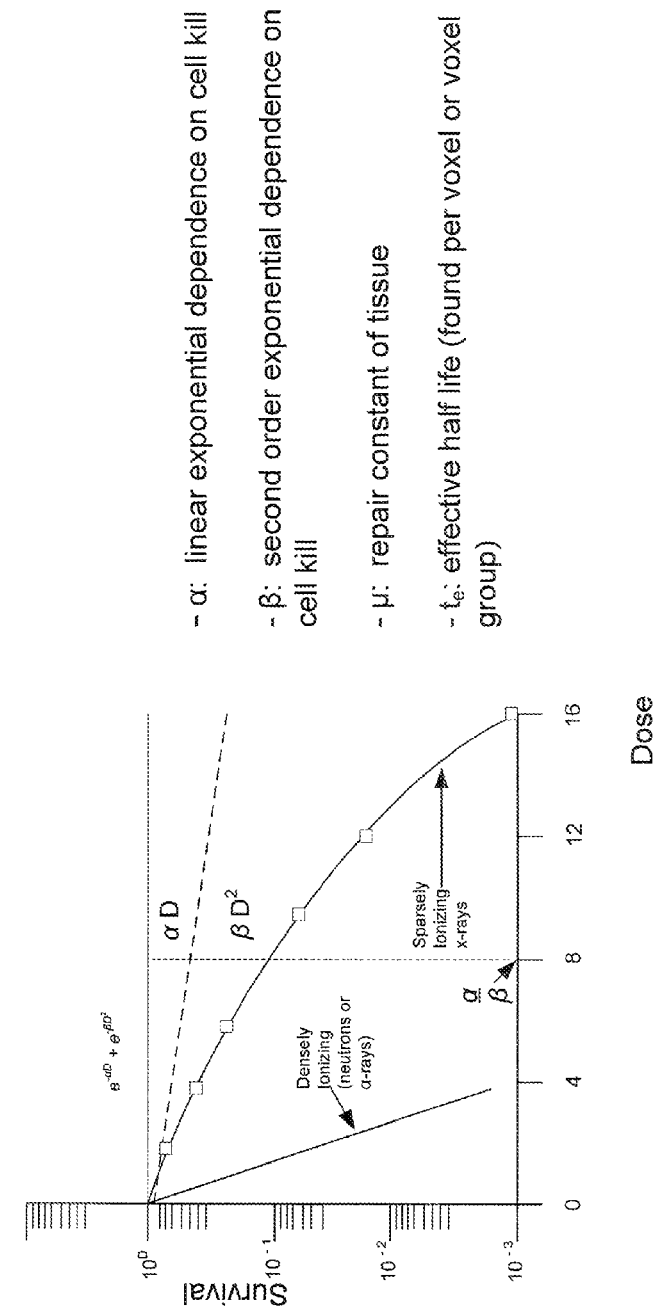
- α: linear exponential dependence on cell kill
- β: second order exponential dependence on cell kill
- μ: repair constant of tissue
- $t_e$: effective half life (found per voxel or voxel group)

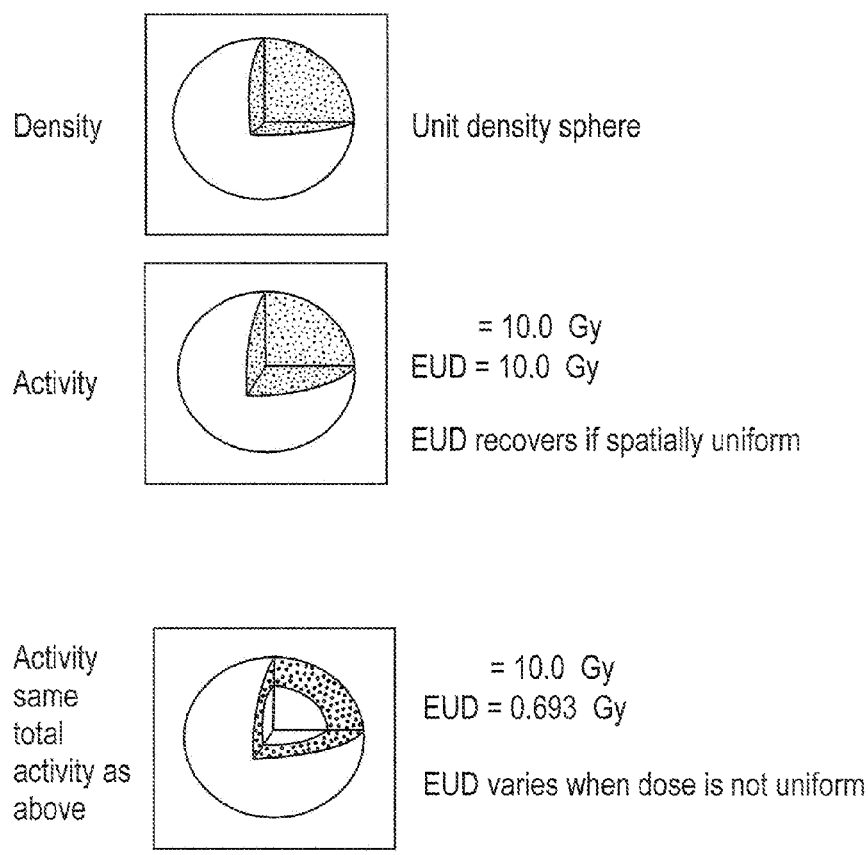
FIGURE 17 - Spatial Activity Distribution

FIGURE 18 - Non-Uniform Clearance

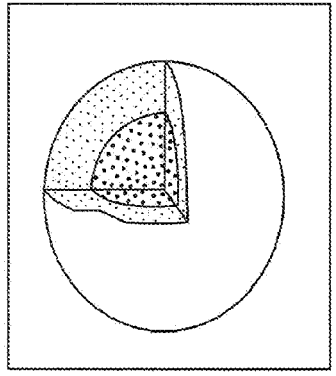

Half-life
Distribution

Lung Tissue
Inner sphere at effective clearance half-life of 4hrs
Outer shell at effective clearance half-life of 2hrs $\bar{D}$ inside   = 10.00 Gy
BED inside  = 13.14 Gy
$\bar{D}$ outside = 10.00 Gy
BED outside = 15.69 Gy

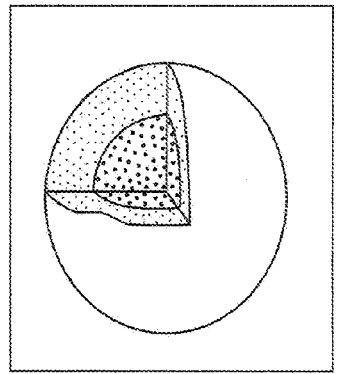

Half-Life
Distribution

Tumor
Inner sphere at effective clearance half-life of 4hrs
Outer shell at effective clearance half-life of 2hrs $\bar{D}$ inside   = 10.00 Gy
BED inside  = 10.09 Gy
$\bar{D}$ outside = 10.00 Gy
BED outside = 11.61 Gy

Spatially Non-Uniform Density Distribution

FIGURE 20 – Clinical Thyroid Case

FIGURE 21

Table 1 – Radiobiological parameters used in the clinical 3D-RD calculation.

|  | α (Gy$^{-1}$) | β (Gy$^{-2}$) | μ (h$^{-1}$) |
|---|---|---|---|
| Lung | .0172 | .00521 | 1.5 |
| Tumor | .365 | .028 | 1.3 |

FIGURE 22

Table 2. – Summary of results from the clinical 3D-RD calculation.

|  | Tumor (Gy) | Lungs (Gy) |
|---|---|---|
| Mean Absorbed Dose | 57.7 | 9.5 |
| Mean BED | 58.5 | 9.8 |
| EUD | 25.0 | 8.3 |

FIGURE 23

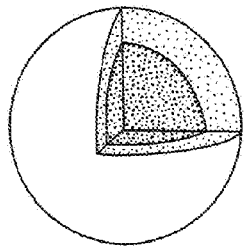

A uniform density sphere with an effective half-life of 2 hours in the outer green region and 4 hours within the red region. Green and red region have equal volume in this example. Initial activity in each region is selected so that total number of decays are equal in both regions.

FIGURE 24

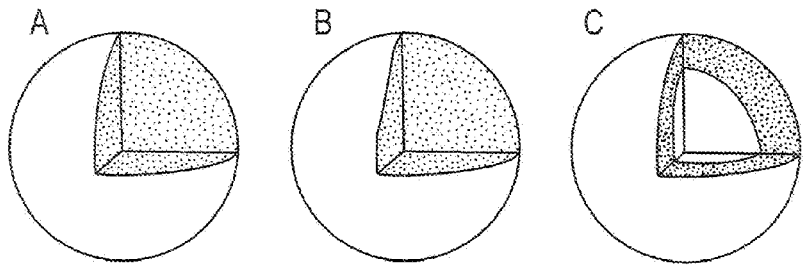

A. Density distribution (uniform) for the uniform (B) and non-uniform (C) activity distribution models; in the non-uniform distribution. The same total activity from 3B is now concentrated into half the volume (the outer shell).

FIGURE 25

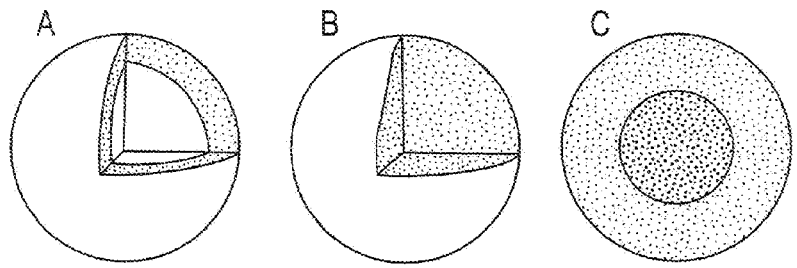

A. Spherical non-uniform density model where inner sphere is twice unit density (2.0 g/cc) and outer shell is at unit density (1.0 g/cc). B. Uniform activity distribution for the density model in Figure 2A. C. Cross sectional slice of 3D-RD output for spherical non-uniform density model.

Clinical CT of patient showing non-uniform density distribution in lungs

Clinical SPECT of patient showing non-uniform activity distribution

Rate map generated from 3 longitudinally aligned SPECT images

Cumulative activity generated from rate map and SPECT

Comparison between Song et al. MCNP based dose volume histogram over lung and tumor regions and the results from EGS using the same inputs. Mean value of MCNP method is Prideaux, et al. 3D-Radiobiological Dosimetry for JNM BED map resulting from 3D-RD using full patient specific data. While the values of AD and BED are different, their relative changes from voxel to voxel are so similar.

Differential absorbed dose (solid line) and BED-volume-histogram (dashed line) of (A) tumor and differential BED-volume-histogram of (B) lung resulting from full patient specific 3D-RD calculation.

METHODS FOR DETERMINING ABSORBED DOSE INFORMATION

This application claims priority to provisional application 60/860,315 filed on Nov. 21, 2006 and also to provisional application 60/860,319, filed on Nov. 21, 2006. Both provisional applications are herein incorporated by reference.

This invention was made with Government support under NIH/NCI grant R01CA116477 and NIH/NCI grant R01CA116477 and DOE grant DE-FG02-05ER63967. The authors also acknowledge. The U.S. Government has certain rights in this invention.

BRIEF DESCRIPTION OF THE FIGURES

FIG. 1 illustrates a method for determining an amount of radioactive material to administer to a patient, according to one embodiment.

FIG. 5 illustrates the output of a 3D-RD calculation, according to one embodiment.

FIG. 6 lists example reference phantom parameter values.

FIG. 8 illustrates DRC values for different $F_{48}$ values.

FIG. 12 depicts example results for the different phantoms at $F_{48}$=0.9 when DRC=20 cGy/h.

FIGS. 16-20 illustrates the use of EUD and BED formulas, according to several embodiments.

FIGS. 21-22 illustrates various parameter values.

FIG. 23 illustrates an example of how an outer shell (with 2 hour half life) is separated from an inner sphere (with 4 hour half life).

FIG. 24 illustrates an example of the impact of dose distribution on EUD.

FIG. 25 illustrates an example of hte impact of dose density on EUD.

DETAILED DESCRIPTION OF EMBODIMENTS OF THE INVENTION

Figure 2:
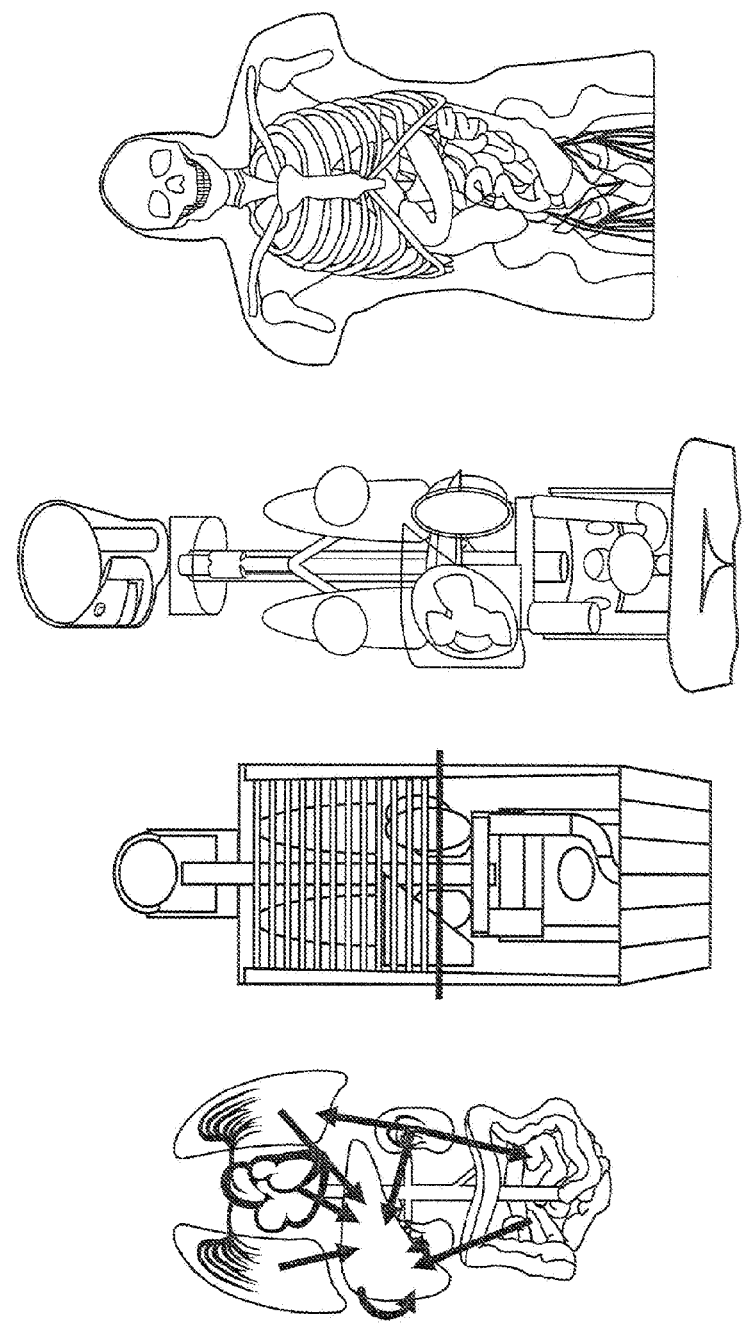
FIG. 2 illustrates different types of models that can be used in determining dose rates for patients.

Utilizing Activity Retention Limit to Obtain Dose Rate

FIG. 1 illustrates details on how an activity retention limit is utilized to obtain the dose rate, according to one embodiment. The resulting dose rate (also referred to as absorbed dose rate) can, for example, make it possible to account for patient-specific differences in determining dose rates for patients. By moving to a dose-rate instead of an activity-based limit on the treatment prescription it is possible to apply well-established and clinically validated constraints on therapy to situations that differ from the original studies used to define these limits. It is also possible to consider the impact of combined, external radiotherapy with targeted radionuclide therapy in determining the optimal amount of radioactivity to administer to a patient. Once a dose-rate has been obtained, it is easier to use many available data sets to assist the patient. The following data sets are examples of data sets that can be utilized: Press et al., *A Phase I/II Trial of Iodine-131-Tositumomab (anti-CD20), Etoposide, Cyclophosphamide, and Autologous Stem Cell Transplantation for Relapsed B-Cell Lymphomas*, Blood, Volume 96, Issue 9, Pages 2934-42 (2000); Ernami et al., *Tolerance of Normal Tissue to Therapeutic Irradiation*, Int. J. Radiation. Oncol. Biol. Phys., Volume 1991, Issue 21, pages 109-122. Those of ordinary skill in the art will see that many other data sets can also be utilized.

Choose Activity Retention Limit

In 105, an activity retention limit is chosen or assumed. This activity retention limit can be assumed based on data sets, such as the Benua-Leeper studies or other studies that have determined the maximum tolerated dose in a patient population. The Benua-Leeper studies have proposed a dosimetry-based treatment planning approach to $^{131}$I thyroid cancer therapy. The Benua-Leeper approach was a result of the observation that repeated $^{131}$I treatment of metastatic thyroid carcinoma with sub-therapeutic doses often fails to cause tumor regression and can lead to loss of iodine-avidity in metastases. The Benua-Leeper study attempted to identify the largest administered $^{131}$I radioactivity that would be safe yet optimally therapeutic. Drawing upon patient studies, the Benua-Leeper study formulated constraints upon the administered activity. For example, the Benua-Leeper study determined that the blood absorbed dose should not exceed 200 rad. This was recognized to be a surrogate for red bone marrow absorbed dose and was intended to decrease the likelihood of severe marrow depression, the dose-limiting toxicity in radioiodine therapy of thyroid cancer. In addition, it was determined that whole-body retention at 48 h should not exceed 120 mCi. This was shown to prevent release of $^{131}$I-labeled protein into the circulation from damaged tumor. Furthermore, in the presence of diffuse lung metastases, it was determined that the 48 h whole-body retention should not exceed 80 mCi. This constraint helped avoid pneumonitis and pulmonary fibrosis. Thus, for example, referring to FIG. 1, in 105, an 80 mCi activity retention limit at 48 h can be assumed based on the Benua-Leeper studies. As shown below, the 48 hr retention limit is converted to a dose-rate limit that can then be used to adjust the 80 mCi to a value that would deliver the same dose-rate for different patient geometries (e.g., pediatric patients)

Determine Dose-Rate in Reference Phantom

In 110 of FIG. 1, utilizing the activity retention limit chosen in 105, S-factors for different phantoms are used to convert the activity retention limit to a dose-rate DRQ). In equation (1) below, a dose-rate DR(t) for lungs at time t in reference phantom P is found:

$$DR^P(t) = A_{LU}(t) \cdot S_{LU \leftarrow LU}^P + A_{RB}(t) \cdot S_{LU \leftarrow RB}^P \quad (1).$$

with:

$$A_{LU}(t) = \frac{A_T \cdot F_T}{e^{-\lambda_{LU} \cdot T}} e^{-\lambda_{LU} \cdot t}, \quad (2)$$

$$A_{RB}(t) = \frac{A_T \cdot (1 - F_T)}{e^{-\lambda_{RB} \cdot T}} e^{-\lambda_{RB} \cdot t}, \quad (3)$$

$$S_{LU \leftarrow RB}^P = S_{LU \leftarrow TB}^P \cdot \frac{M_{TB}^P}{(M_{TB}^P - M_{LU}^P)} - S_{LU \leftarrow LU}^P \cdot \frac{M_{LU}^P}{(M_{TB}^P - M_{LU}^P)}, \quad (4)$$

$A_{LU}(t)$ lung activity at time t, $S_{LU \leftarrow LU}^P$ lung to lung $^{131}$I S-factor for reference phantom, P, $A_{RB}(t)$ remainder body activity (total-body-lung) at time, t, $S_{LU \leftarrow RB}^P$ remainder body to lung $^{131}$I S-factor for reference phantom, P, $A_T$ whole-body activity at time, T, $F_T$ fraction of $A_T$ that is in the lungs at time, T, $\lambda_{LU}$ effective clearance rate from lungs (=ln(2)/$T_E$; with $T_E$=effective half-life), $\lambda RB$ effective clearance rate from remainder body (=ln(2)/$T_{RB}$, with $T_{RB}$=effective half-life in remainder body), $S_{LU \leftarrow TB}^P$ total-body to lung $^{131}$I S-factor for reference phantom. P, $M_{TB}^P$ total-body mass of reference phantom. P, $M_{LU}^P$ lung mass of reference phantom. P.

Equation (2) describes a model in which radioiodine uptake in tumor-bearing lungs is assumed instantaneous relative to the clearance kinetics. Clearance is modeled by an exponential expression with a clearance rate constant, $\lambda_{LU}$, and corresponding effective half-life, $T_E$. At a particular time, T, after administration, the fraction of whole-body activity that is in the lungs is given by the parameter, $F_T$. Activity that is not in the lungs (i.e., in the remainder body (RB)) is also modeled by an exponential clearance (Equation (3)), but with a different rate constant, $\lambda_{RB}$. At time, T, the fraction of whole-body activity in this compartment is 1-$F_T$. Equation (4) can be obtained from the following reference: Loevinger et al., *MIRD Primer for Absorbed Dose Calculations, Revised Edition.*, The Society of Nuclear Medicine, Inc. (1991).

Using equations (2) and (3) to replace $A_{LU}(t)$ and $A_{RB}(t)$ in equation 1, the dose rate to lungs at time, T, for phantom, P, is:

$$DR^P(T) = A_T F_T \cdot S_{LU \leftarrow LU}^P + A_T (1 - F_T) \cdot S_{LU \leftarrow RB}^P \quad (5).$$

Derived Activity Constraint

In 115, once we have the dose-rate at a certain time (e.g., 48 h) as the relative constraint for a certain phantom, then dose-rate constraints (DRCs) at this same time (e.g., 48 h) can be derived for different reference phantoms. Thus, for example, If we assume that the dose-rate to the lungs at 48 h is the relevant constraint on avoiding prohibitive lung toxicity, then, one may derive 48-hour activity constraints for different reference phantoms that give a 48 h dose rate equal to a pre-determined fixed dose rate constraint, denoted, DRC. By re-ordering expression 5 and renaming $A_T$ to $A_{DRC}^P$, the activity constraint for phantom P so that $DR^P(48h)$=DRC, we get:

$$A_{DRC}^P = \frac{DRC}{F_{48} \cdot S_{LU \leftarrow LU}^P + (1 - F_{48}) \cdot S_{LU \leftarrow RB}^P}. \quad (6)$$

In equation 6, $A_{DRC}^P$, depends upon the fraction of whole-body activity in lungs at 48 hours and also on the reference phantom that best matches the patient characteristics.

Corresponding Administered Activity

In 120, once we have the dose rate constraints for different phantoms, corresponding administered activity can be found for those phantoms. Equation (6) gives the 48 hour whole-body activity constraint so that the dose rate to lungs at 48 hours does not exceed DRC. The corresponding constraint on the maximum administered activity, $AA_{max}$, can be derived by using equations 2 and 3, to give an expression for the total-body activity as a function of time:

$$A_{TB}(t) = \frac{A_T \cdot F_T}{e^{-\lambda_{LU} \cdot T}} e^{-\lambda_{LU} \cdot t} + \frac{A_T \cdot (1 - F_T)}{e^{-\lambda_{RB} \cdot T}} e^{-\lambda_{RB} \cdot t}. \quad (7)$$

Replacing $A_T$ with $A_{DRC}^P$ and setting t=0, the following expression is obtained for $AA_{max}$:

$$AA_{max} = \frac{A_{DRC}^P \cdot F_{48}}{e^{-\lambda_{LU} \cdot 48}} + \frac{A_{DRC}^P \cdot (1 - F_{48})}{e^{-\lambda_{RB} \cdot 48}}. \quad (8)$$

The denominator in each term of this expression scales the activity up to reflect the starting value needed to obtain $A_{TB}$ (48 h)=$A_{DRC}^P$. $AA_{max}$ is shown to be dependent on $\lambda_{LU}$, and $\lambda_{RB}$ (or equivalently on $T_E$ and $T_{RB}$).

Mean Lung Absorbed Dose

In 125, the mean absorbed dose may be obtained by integrating the dose rate from zero to infinity. Thus, the mean lung absorbed does can be obtained by integrating equation (1) from 1 to infinity:

$$DLU = \tilde{A}_{LU} \cdot S_{LU \leftarrow LU}^P + \tilde{A}_{RB} \cdot S_{LU \leftarrow RB}^P \quad (9).$$

Integrating the expressions for lung and remainder body activity as a function of time, (equations (2) and (3), respectively) and replacing parameters with the 48 hour constraint values the following expressions are obtained for $\tilde{A}_{LU}$ and $\tilde{A}_{RB}$:

$$\tilde{A}_{LU} = \frac{A_{DRC}^P \cdot F_{48} \cdot e^{\frac{\ln(2)}{T_E}T}}{\ln(2)} \cdot T_E, \quad (10)$$

$$\tilde{A}_{RB} = \frac{A_{DRC}^P \cdot (1 - F_{48}) \cdot e^{\frac{\ln(2)}{T_{RB}}T}}{\ln(2)} \cdot T_{RB}. \quad (11)$$

In equations (10) and (11), the $\lambda$ values have been replaced to explicitly show the dependence of the cumulated activities on the clearance half-lives.

If $T_{RB}$ is kept constant and $T_E$ is varied, the minimum absorbed dose to the lungs will occur at a $T_E$ value that gives a minimum for equation (9). This can be obtained by differentiating with respect to $T_E$, setting the resulting expression to zero and solving for $T_E$. This gives $T_E$=ln(2)·48 h=33 h.

Electron v. Photon Contribution to the Lung Dose

Since almost all of the activity in tumor-bearing lungs would be localized to tumor cells, it is instructive to separate the electron contribution to the estimated lung dose from the photon contribution. The electron contribution would be expected, depending upon the tumor geometry (II), to irradiate tumor cells predominantly, while the photon contribution will irradiate lung parenchyma. The dose contribution from the remainder body is already limited to photon emissions. The photon only lung to lung S-value ($SP^P_{LU \leftarrow LU}$) for a phantom, P, is obtained from the S-factor value and the delta value for electron emissions of $^{131}$I:

$$SP^P_{LU \leftarrow LU} = S^P_{LU \leftarrow LU} - \frac{\Delta^{131I}_{electron}}{M^P_{LU}}, \quad (12)$$

$\Delta_{electron}{}^{131I}$ Total energy emitted as electrons per disintegration of $^{131}$I. Replacing $SP^P_{LU \leftarrow LU}$ for $S^P_{LU \leftarrow LU}$ in equation 9 gives the absorbed dose to lungs from photon emissions only.

Parameter Values

The table in FIG. 6 lists the reference phantom parameter values used in the calculations. The masses, lung-to-lung and total body-to-lung S-values listed were obtained from the OLINDA dose calculation program. The remainder body (RB)-to-lung and lung-to-lung photon-only S values were calculated using equations (4) and (12), respectively. The effective clearance half-life of radioiodine activity not localized to the lungs, $T_{RB}$, was set to 10 or 20 h. These values correspond to reported values for whole-body clearance with or without recombinant TSH, respectively. The effective clearance half-life for activity in tumor-bearing lungs, $T_E$, was varied from 20 to 100 h. The fraction of whole-body activity in the lungs at 48 h, $F_{48}$, was varied from 0.6 to 1.

EXAMPLE

Figure 7:
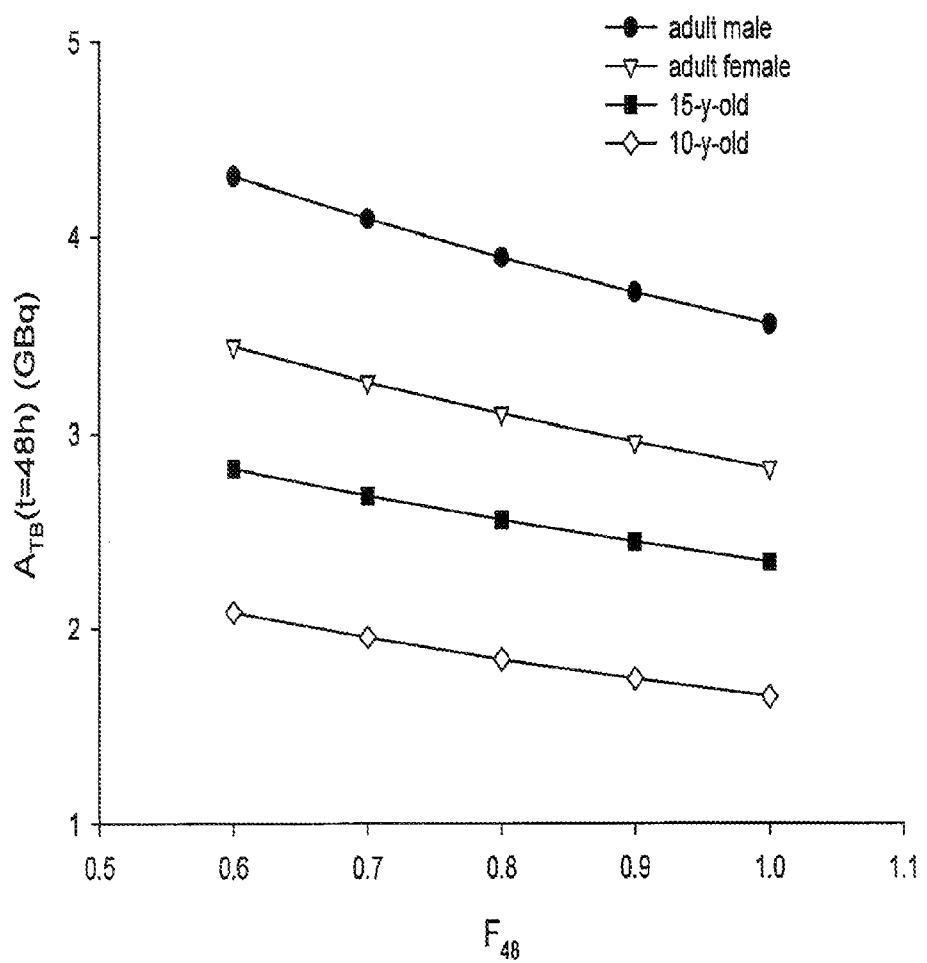
FIG. 7 provides example 48 h whole-body activity retention values for different phantoms and $F_{48}$ values.

To derive the dose-rate to lungs associated with the 80 mCi, 48 h constraint we assume that 90% of the whole-body activity is uniformly distributed in the lungs ($F_{48}$=0.9). The original reports describing the 80 mCi, 48 h limit do not provide a value for this parameter; the value chosen is consistent with the expected biodistribution in patients with disease that is dominated by diffuse lung metastases. As noted above, the 80 mCi activity constraint was derived primarily from results obtained in females. Accordingly, the conversion from activity to dose-rate is performed using S-factors and masses for the adult female phantom. Using equation, (5), with $F_{48}$=0.9, the dose-rate constraint (DRC) corresponding to the 48 h, 80 mCi limit is 41.1 cGy/h. This is the estimated dose-rate to the lungs when 80 mCi of $^{131}$I are uniformly distributed in the lungs of an adult female whose anatomy is consistent with the standard female adult phantom geometry. Implicit in the 80 mCi at 48 h constraint is that radiation induced pneumonitis and pulmonary fibrosis will be avoided as long as the dose-rate is not in excess of 41.1 cGy/h at 48 h after $^{131}$I administration. If we assume that this dose-rate based constraint applies to pediatric patients, then using equation 6, we may calculate the 48 h activity limitation if the patient anatomy is consistent with the 15 or 10 year-old standard phantom. FIG. 7 provides the 48 h whole-body activity retention values for different phantoms and $F_{48}$ values. Since the guidelines were developed with data from females, the 80 mCi rule applied to adult males gives a 48 h whole-body activity constraint of 3.73 GBq (101 mCi) at $F_{48}$=0.9; corresponding values for the 15-year old and 10-year old phantoms are 2.46 GBq (66.4 mCi) and 1.73 GBq (46.7 mCi). It is important to note that because it is a dose-rate, DRC, does not depend upon the clearance parameters. The value chosen, does, however, depend upon the assumed lung fraction of whole-body activity. FIG. 8 lists the DRC values for different $F_{48}$ values. All of the results presented will scale linearly by DRC value.

Figure 9:
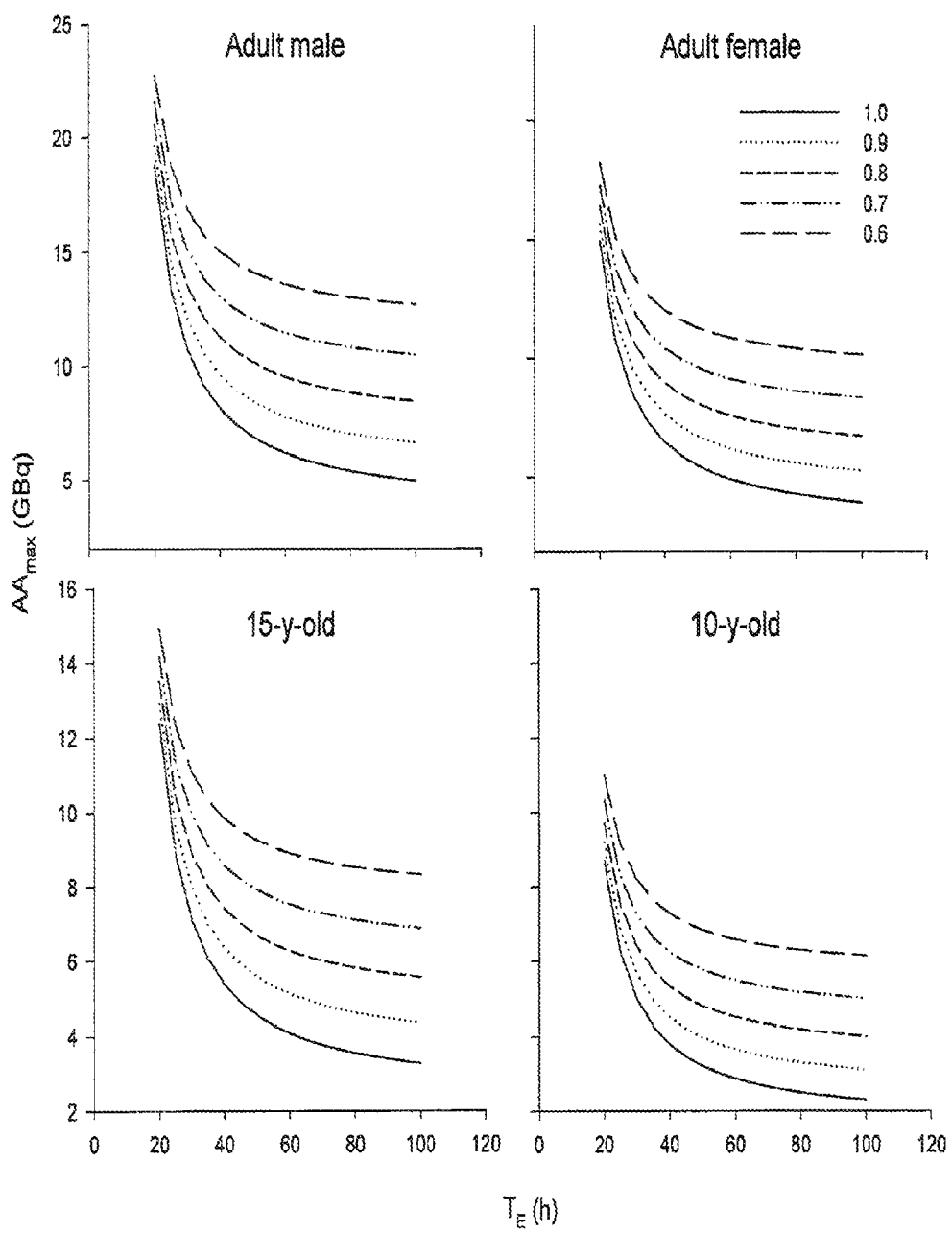
FIG. 9 depicts examples of administered activity limits for different phantoms and $F_{48}$ values as a function of $T_E$ when $T_{RB}$ is set to 20 h.
Figure 10:
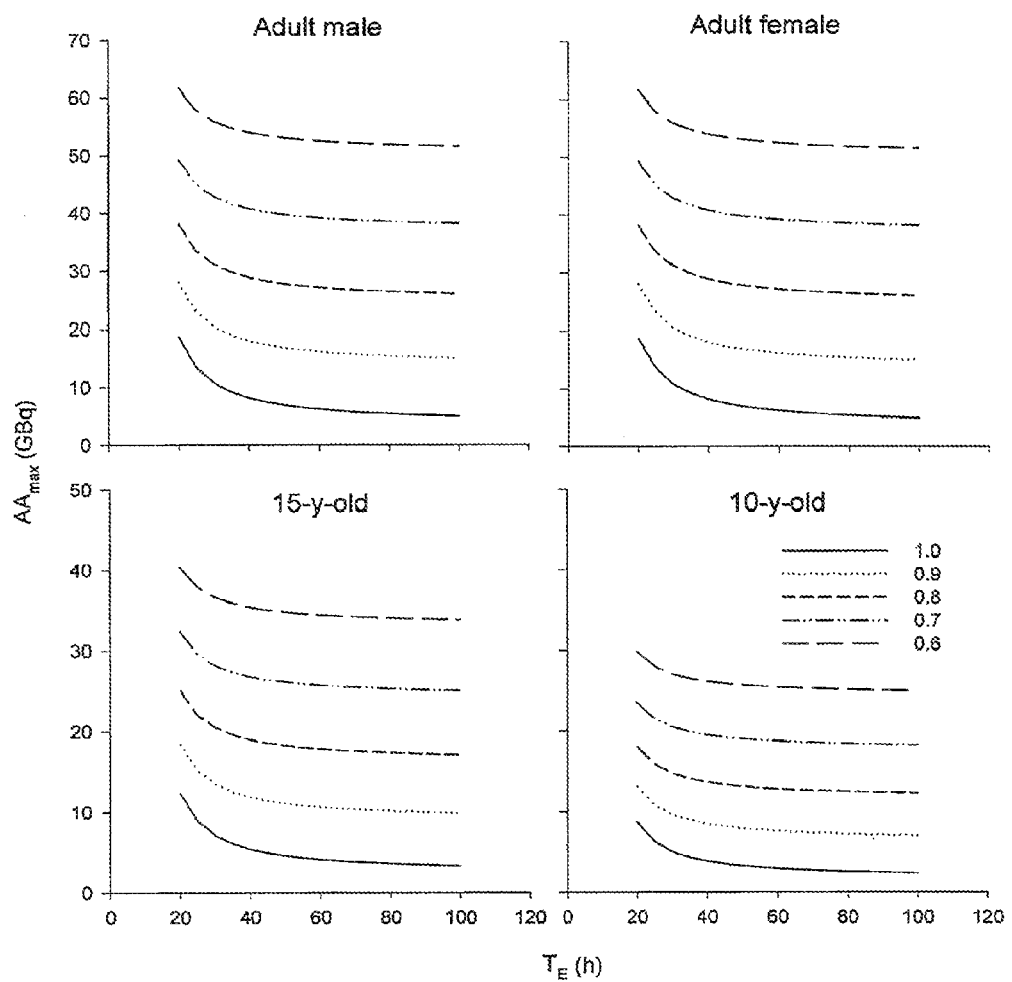
FIG. 10 depicts example corresponding results when $T_{RB}$ equals 10 h.

The majority of patients with diffuse $^{131}$I-avid lung metastases exhibit prolonged whole-body retention. In such cases, the whole-body kinetics are dominated by tumor-associated activity. Assuming that 90% of the whole-body activity is in the lungs and that this clears with an effective half-life of 100 h, while the remainder activity clears with an effective half-life of 20 h (corresponding to a treatment plant that includes hormone withdrawal), equation (8) may be used to calculate the administered activity that will yield the corresponding 48 h activity constraint for each phantom. The administered activity values are 6.64, 5.23, 4.37 and 3.08 GBq (180, 143, 118 and 83.2 mCi), respectively, for adult male, female, 15 year old and 10 year old standard phantom anatomies. These values depend on the assumed clearance half life of activity in the remainder of the body. If an effective half-life of 10 h (consistent with use of recombinant human TSH (rhTSH)) is assumed, the corresponding administered activity values are: 15.1, 12.0, 9.92 and 6.98 GBq (407, 323, 268 and 189 mCi). FIG. 9 depicts administered activity limits for different phantoms and $F_{48}$ values as a function of $T_E$ when $T_{RB}$ is set to 20 h. FIG. 10 depicts corresponding results when $T_{RB}$ equals 10 h. The plots show that at $T_E$ greater than three to four times $T_{aRB}$ the administered activity limit is largely independent of lung clearance half-life but, as shown by the equidistant spacing of the curves with increasing $F_{48}$, remains linearly dependent on the fraction of whole-body activity that is in the lungs at 48 h. When $T_E$ approaches the lower $T_{RB}$ value as in FIG. 9, $AA_{max}$ increases rapidly and appears to converge. This reflects the condition of a partitioned activity distribution that clears from lungs and remainder body at the same effective half-life; the AA values at $T_E=T_{RB}=20$ h are not the same because the dose-rate, which is used to determine $AA_{max}$ will be different due to the physical distribution of the activity even when the half-lives are the same. The rapid increase in $AA_{max}$ at lower $T_E$ values reflects the need to increase patient administered activity as the clearance rate increases.

Figure 11:
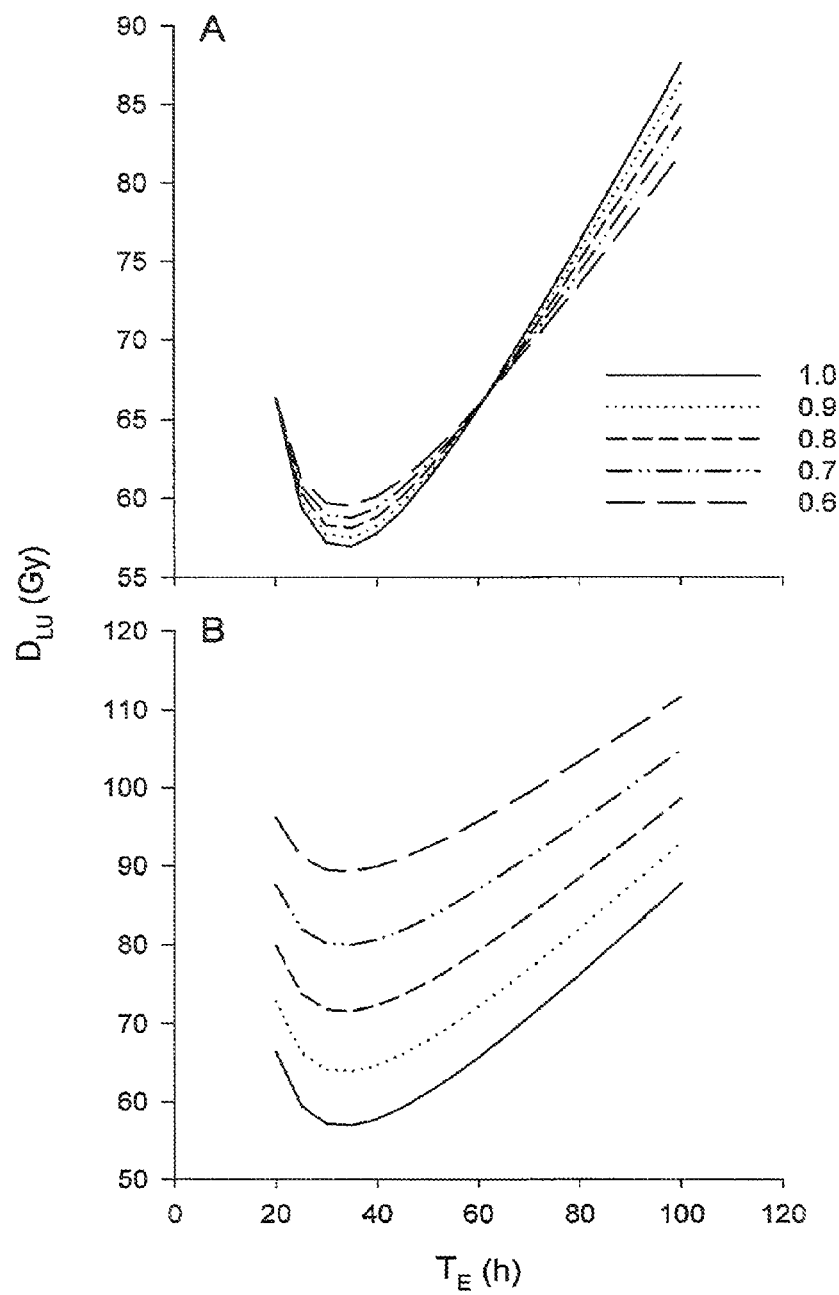
FIG. 11 depicts examples of absorbed dose to lungs as a function of $T_E$ for different $F_{48}$ values.

FIG. 11 depicts the absorbed dose to lungs as a function of $T_E$ for different $F_{48}$ values. Since the administered activities are adjusted to reach a constant 48 h dose-rate in lungs, the absorbed dose curves are essentially independent of phantom geometry with less than 2% difference in lung absorbed dose vs $T_E$ profiles across the 4 standard phantom geometries (data not shown). Both sets of curves show a minimum absorbed dose at $T_E$=33.3 h (=ln(2)×48 h). The minimum absorbed dose is 53.6 Gy for $T_{RB}$=20 h and ranges from 53.6 ($F_{48}$=1) to 54.2 Gy ($F_{48}$=0.6) for $T_{RB}$=10 h.

Less is known regarding the effects of lung irradiation on pediatric patients or patients with already compromised lung function. In such cases a more conservative dose-rate limit may be appropriate. As noted earlier, the results shown in FIGS. 7, and 9-11 scale linearly with DRC, the table in FIG. 12 summarizes the relevant results for the different phantoms at $F_{48}$=0.9 when DRC=20 cGy/h. In the adult female phantom, this corresponds to 1.44 GBq (38.9 mCi) retained in the whole body at 48 h.

Figure 13:
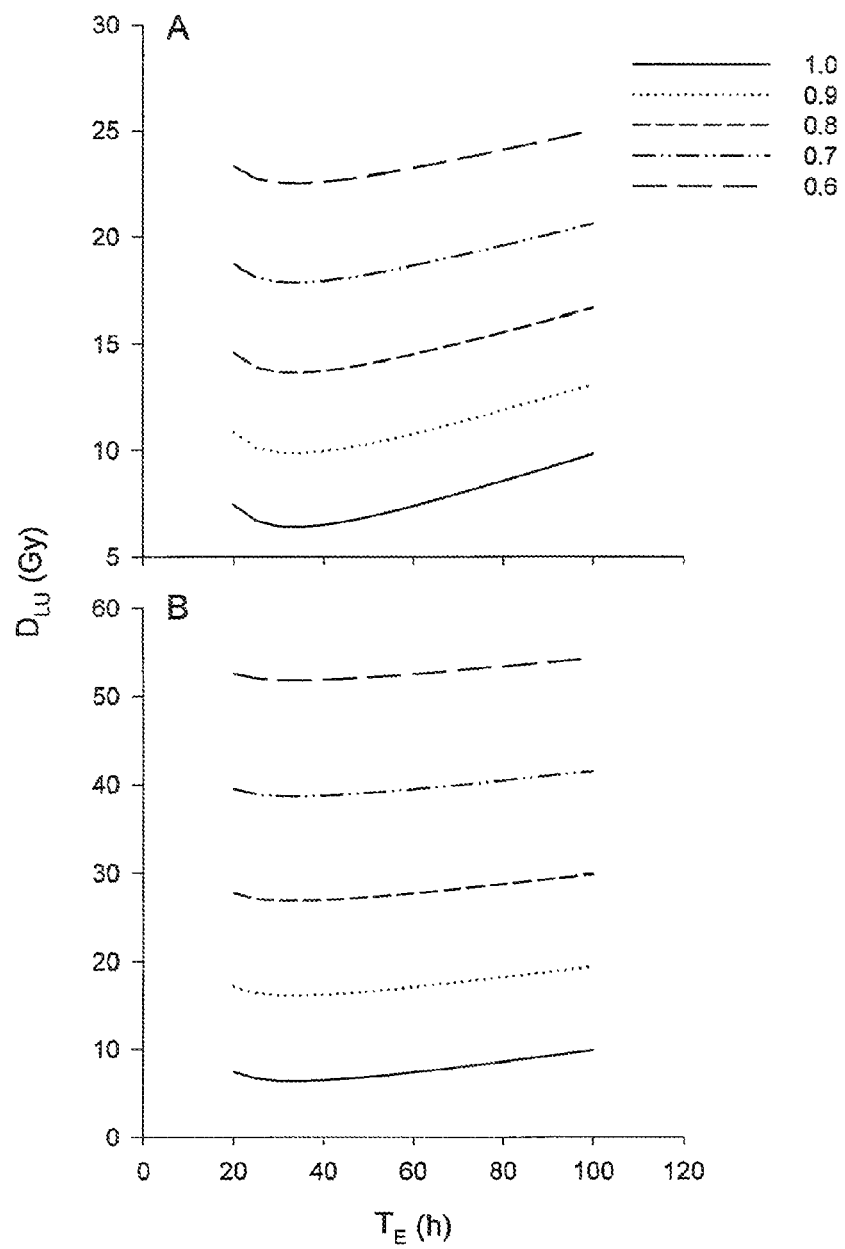
FIGS. 13A and 13B illustrates absorbed dose v. $T_E$ curves for adult female phantom and for two different remainder body effective clearance half-lives.

All of the lung absorbed dose values shown on FIG. 11 and listed in the table in FIG. 12 are well above the reported 24 to 27 Gy MTD for adult lungs. The discrepancy may be explained by considering the photon and electron fraction of this absorbed dose. The electron emissions are deposited locally, most likely within the thyroid carcinoma cells that have invaded the lungs, while the photon contribution would irradiate the total lung volume. Using equations (9) and (12), the lung absorbed dose attributable to photons may be calculated. Absorbed dose vs $T_E$ curves are depicted in FIGS. 13A and 13B for the adult female phantom and for the two different remainder body effective clearance half-lives considered. The photon absorbed dose is less dependent upon clearance of lung activity (i.e., $T_E$) and more dependent on remainder body clearance. Comparing FIG. 13A with FIG. 13B, there is a greater than two-fold increase in the photon absorbed dose as the clearance rate is doubled and $F_{48}$=0.6. The increase depends upon the spatial distribution so that at $F_{48}$=0.9, the dose increases by a factor of 1.6.

Unlike the total dose, the photon dose is also more heavily dependent upon the phantom. At $T_E$=100 h, the photon lung dose to the adult male ranges from 8.75 ($F_{48}$=1.0) to 9.03 ($F_{48}$=0.6) Gy when $T_{RB}$=20 h; the corresponding values when $T_{RB}$=10 h, are 8.75 ($F_{48}$=1.0) and 9.56 ($F_{48}$=0.6) Gy. In the 15-year-old, the corresponding values are: 7.85, 8.10, 7.85 and 8.55 Gy; corresponding values for the 10-year-old are: 7.09, 7.33, 7.09 and 7.78 Gy.

3D-RD (3D-Radiobiological Dosimetry)

In one embodiment, a method is provided that incorporates radiobiological modeling to account for the spatial distribution of absorbed dose and also the effect of dose-rate on biological response. The methodology is incorporated into a software package which is referred to herein as 3D-RD (3D-Radiobiological Dosimetry). Patient-specific, 3D-image based internal dosimetry is a dosimetry methodology in which the patient's own anatomy and spatial distribution of radioactivity over time are factored into an absorbed dose calculation that provides as output the spatial distribution of absorbed dose.

Figure 3:
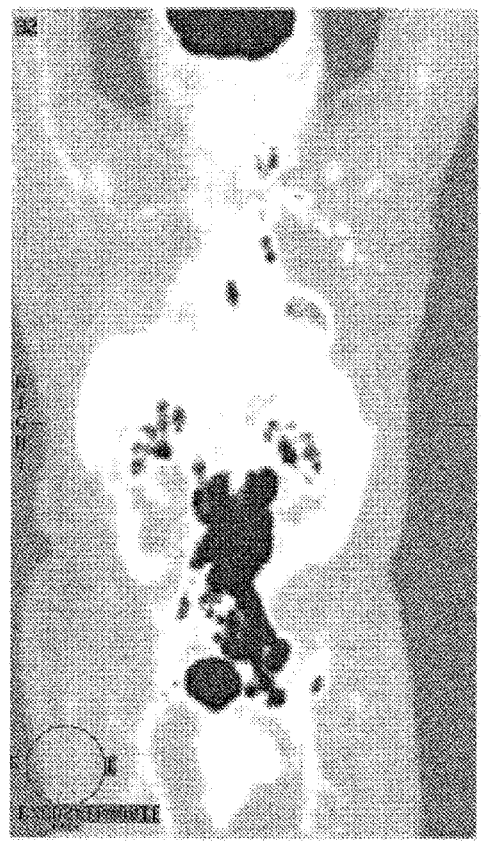
FIGS. 3-4 illustrate examples of actual images of patients.
Figure 4:
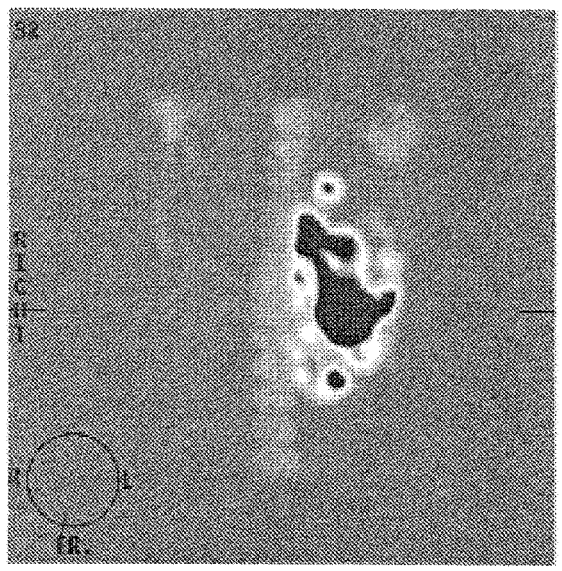
Figure 14:
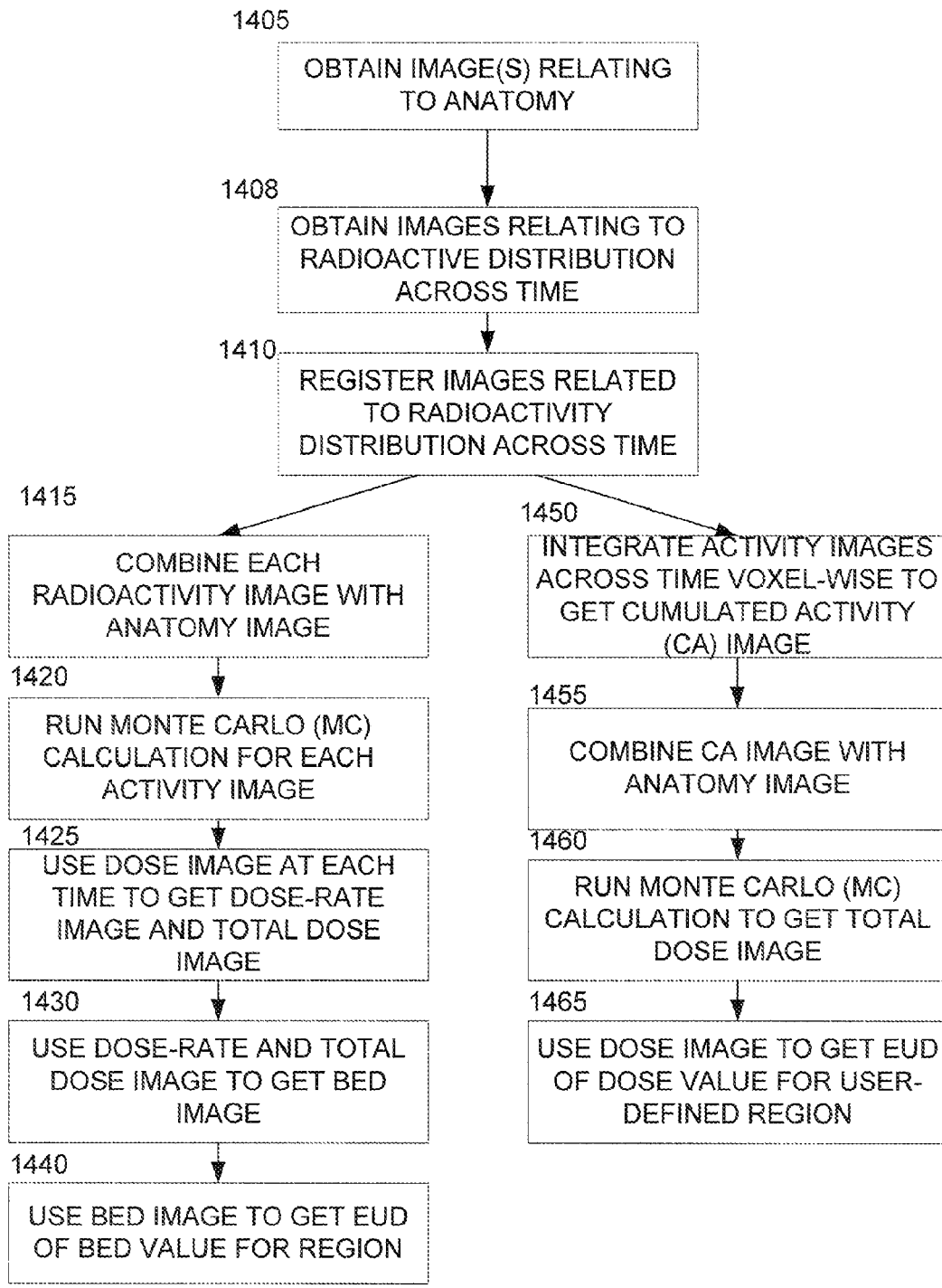
FIG. 14 illustrates a method for a 3D-RD calculation, according to one embodiment.
Figure 15A:
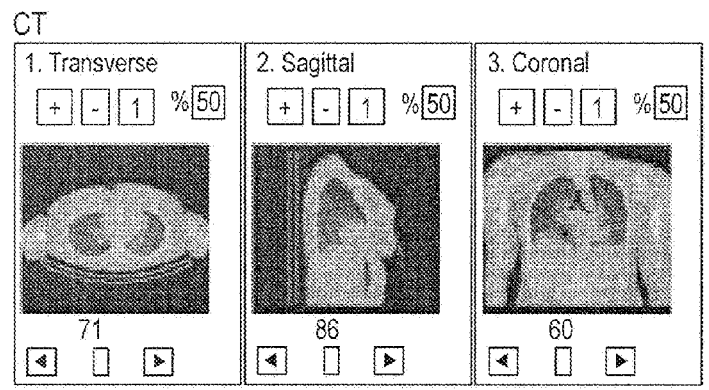
FIG. 15A illustrates an example of computed tomography (CT) images.
Figure 15B:
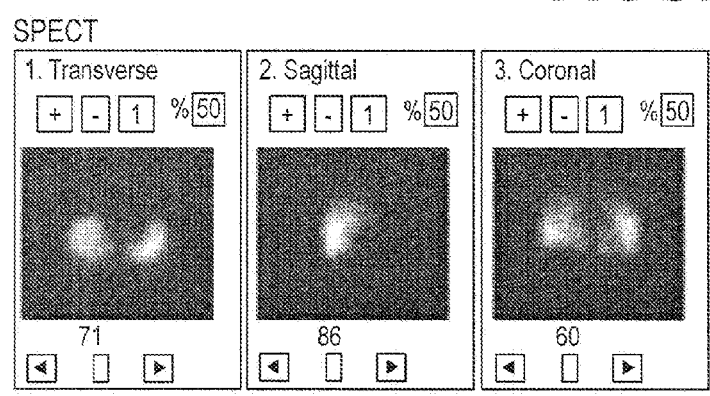
FIG. 15B illustrates an example of positron emission tomography (PET) images.

FIGS. 3-4 illustrate actual images of patients. FIG. 5 illustrates the output of a 3D-RD calculation. FIG. 14 sets forth a method for a 3D-RD calculation. Referring to FIG. 14, in 1405, anatomical images of the patient are obtained. For example, one or more computed tomography (CT) images, such as the images illustrated in FIG. 15A, one or more single photon emission computed tomography (SPECT) images, such as the images illustrated in FIG. 15B, and/or one or more positron emission tomography (PET) images can be input. A CT image can be used to provide density and composition of each voxel for use in a Monte Carlo calculation. A CT image can also be used to define organs or regions of interest for computing spatially averaged doses. For example, a CT image can show how a tumor is distributed in a particular organ, such as a lung. A longitudinal series of PET or SPECT images can be used to perform a voxel-wise time integration and obtain the cumulated activity or total number of disintegrations on a per voxel basis. If multiple SPECT or PET studies are not available, a single SPECT or PET can be combined with a series of planar images. By assuming that the relative spatial distribution of activity does not change over time, it is possible to apply the kinetics obtained from longitudinal planar imaging over a tumor or normal organ volume to the single SPECT or PET image, thereby obtaining the required 3-D image of cumulated activity. The results of such a patient-specific 3-D imaging-based calculation can be represented as a 3-D parametric image of absorbed dose, as dose-volume histograms over user-defined regions of interest or as the mean, and range of absorbed doses over such regions. Such patient-specific, voxel-based absorbed dose calculations can help better predict biological effect of treatment plans. The approach outlined above provides estimated total absorbed dose for each voxel, collection of voxels or region. An alternative approach that makes it easier to obtain radiobiological parameters such as the biologically effective dose (BED) is to estimate the absorbed dose for each measure time-point and then perform the voxel-wise time integration to get the total absorbed dose delivered. This approach makes it easier to calculate dose-rate parameters on a per voxel basis which are needed for the BED calculation.

In 1408, images are obtained relating to radioactive distribution across time.

Figure 15C:
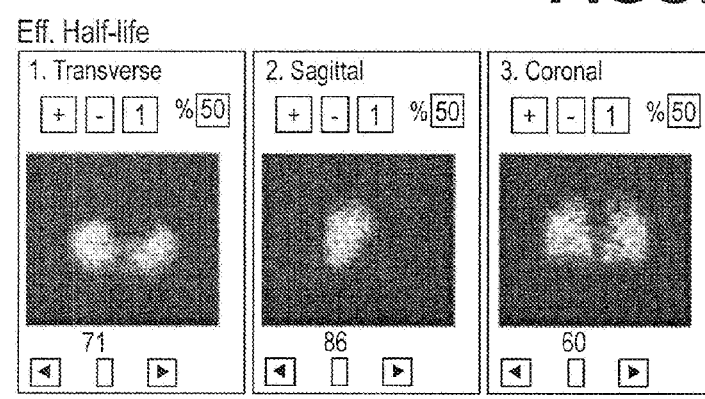
FIG. 15C illustrates an example of kinetic parameter images.
Figure 19:
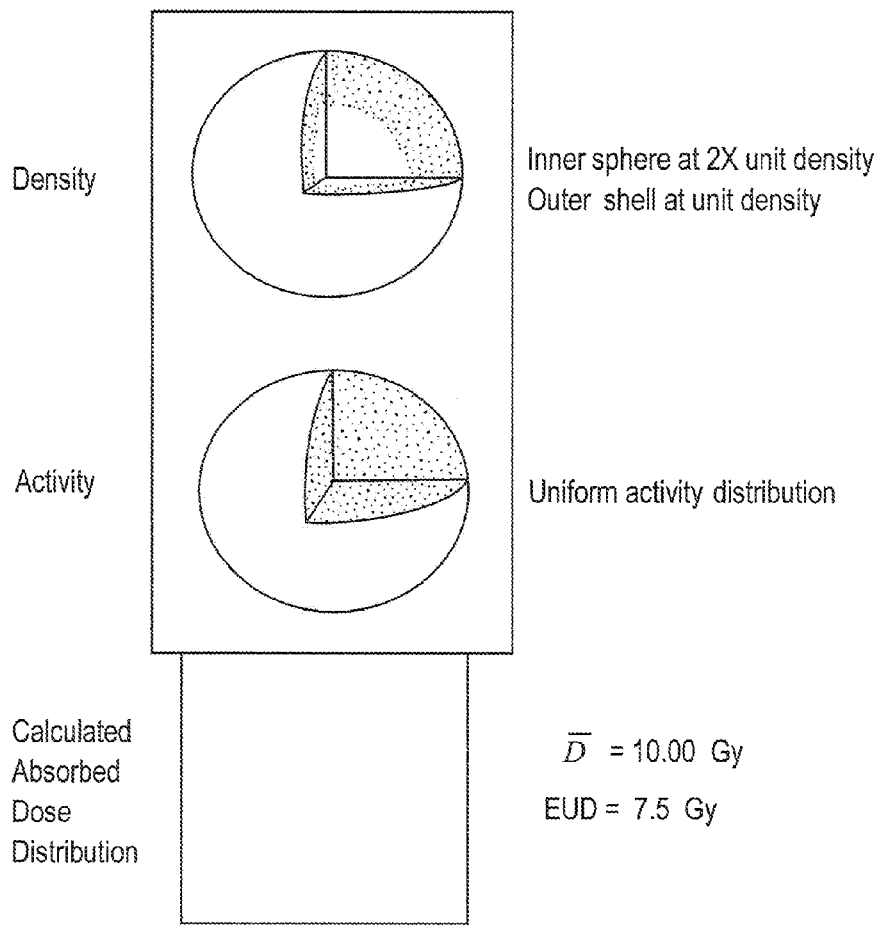
Figure 20:
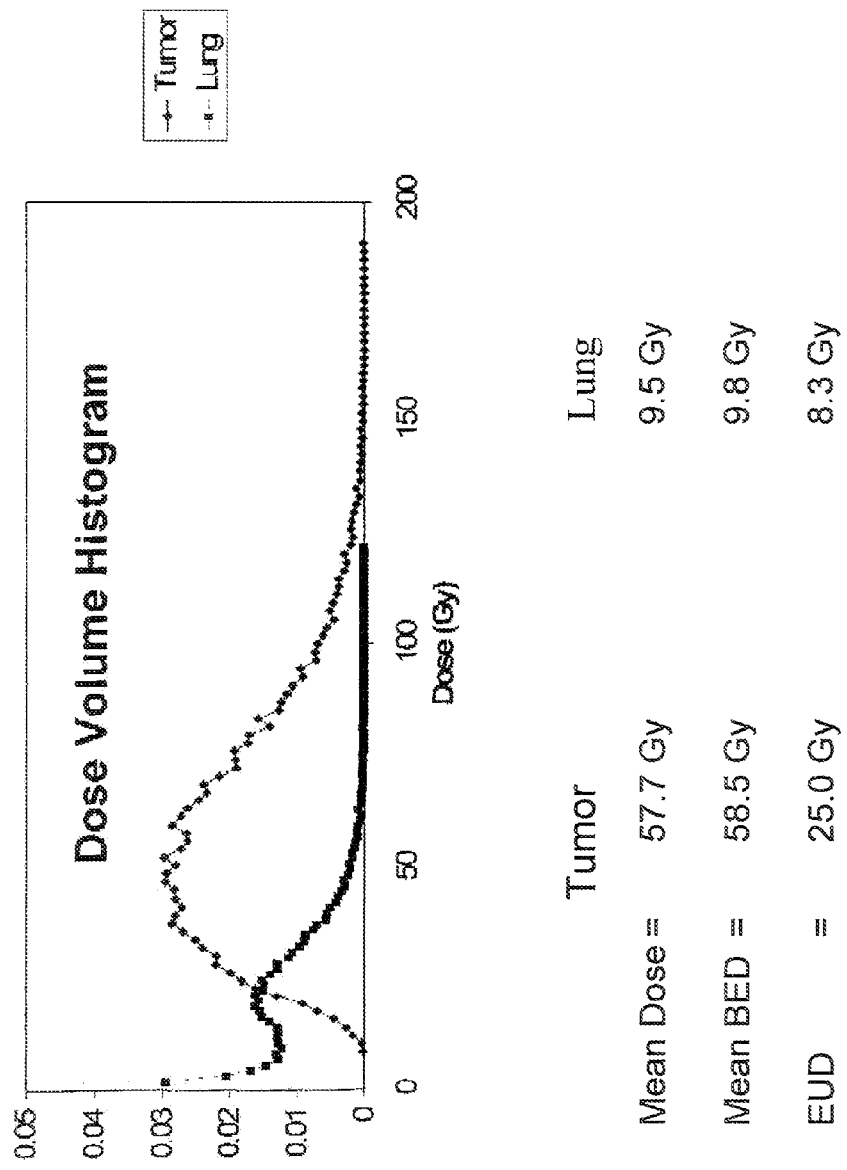

FIG. 15C illustrates an example of kinetic parameter images; in this case the effective half-life for each voxel is displayed in a color-coded image. These kinetic parameter images provide an estimate of clearance rate of the radiological material in each voxel in a 3D image.

In 1410, the images related to the radioactive distribution are registered across time. At this point, one of at least two options (1415-1440 or 1450-1465) can be followed. In 1415, each radioactivity image can be combined with an anatomy image. The anatomical image voxel values can be utilized to assign density and composition (i.e., water, air and bone).

In 1420, Monte Carlo simulations are nm on each activity image. Thus, the 3-D activity image(s) and the matched anatomical image(s) can be used to perform a Monte Carlo calculation to estimate the absorbed dose at each of the activity image collection times by tallying energy deposition in each voxel.

In 1425, the dose image at each point in time is used to obtain a dose-rate image and a total dose image.

In 1430, the dose-rate and the total dose image are utilized to obtain the BED image. In 1440, the BED image is utilized to obtain the EUD of BED value for a chosen anatomical region.

In the other option, after 1410, activity images can be integrated across time voxel-wise to obtain a cumulated activity (CA) image. In 1455, the CA image is combined with an anatomy image. In 1460, a Monte Carlo (MC) calculation is run to get the total dose image. In 1465, the dose image is utilized to obtain the EUD of the dose value for a chosen anatomical region.

EUD and BED formulas (as described in more detail below and also illustrated in FIGS. 16-20) can be utilized to incorporate the radiological images into the anatomical image(s). The spatial absorbed dose distribution can be described by the equivalent uniform dose (EUD, defined on a per structure basis). The rate at which the material is delivered can be described by the biologically effective dose (BED, defined on a per voxel basis).

EUD and BED

The uniformity (or lack thereof) of absorbed dose distributions and their biological implications have been examined. Dose-volume histograms have been used to summarize the large amount of data present in 3-D distributions of absorbed dose in radionuclide dosimetry studies. The EUD model introduces the radiobiological parameters, $\alpha$ and $\beta$, the sensitivity per unit dose and per unit dose squared, respectively, in the linear-quadratic dose-response model. The EUD model converts the spatially varying absorbed dose distribution into an equivalent uniform absorbed dose value that would yield a biological response similar to that expected from the original dose distribution. This provides a single value that may be used to compare different dose distributions. The value also reflects the likelihood that the magnitude and spatial distribution of the absorbed dose is sufficient for tumor kill.

It is known that dose rate influences response. The BED formalism, sometimes called Extrapolated Response Dose, was developed to compare different fractionation protocols for external radiotherapy. BED may be thought of as the actual physical dose adjusted to reflect the expected biological effect if it were delivered at a reference dose-rate. As in the case of EUD, by relating effects to a reference value, this makes it possible to compare doses delivered under different conditions. In the case of EUD the reference value relates to spatial distribution and is chosen to be a uniform distribution. In the case of BED the reference value relates to dose rate and is chosen to approach zero (total dose delivered in an infinite number of infinitesimally small fractions).

As described above with respect to 1415, the patient-specific anatomical image(s) are combined with radioactivity images into paired 3D data sets. Thus, the anatomical image voxel values can be utilized to assign density and composition (i.e., water, air and bone). This information, coupled with assignment of the radiobiological parameters, $\alpha$, $\beta$, $\mu$, the radiosensitivity per unit dose, radiosensitivity per unit dose squared and the repair rate assuming an exponential repair process, respectively, is used to generate a BED value for each voxel, and subsequently an EUD value for a particular user-defined volume.

In external radiotherapy, the expression for BED is:

$$BED = Nd\left(1 + \frac{d}{\alpha/\beta}\right). \quad (1)$$

This equation applies for N fractions of an absorbed dose, d, delivered over a time interval that is negligible relative to the repair time for radiation damage (i.e., at high dose rate) where the interval between fractions is long enough to allow for complete repair of repairable damage induced by the dose d; repopulation of cells is not considered in this formulation but there are formulations that include this and this could easily be incorporated in embodiments of the present invention. The parameters, $\alpha$ and $\beta$ are the coefficients for radiation damage proportional to dose (single event is lethal) and dose squared (two events required for lethal damage), respectively.

A more general formulation of equation (1) is:

$$BED(T) = D_T(T) \cdot RE(T) \quad (2),$$

where BED(T) is the biologically effective dose delivered over a time T, $D_T(T)$ is the total dose delivered over this time and RE(T) is the relative effectiveness per unit dose at time, T. The general expression for RE(T) assuming a time-dependent dose rate described by D(t) is given by:

$$RE(T) = 1 + \frac{2}{D_T(T)\left(\frac{\alpha}{\beta}\right)} \times \int_0^T dt \cdot D(t) \int_0^t dw \cdot D(w) e^{-\mu(t-w)}. \quad (3)$$

The second integration over the time-parameter, w, represents the repair of potentially lethal damage occurring while the dose is delivered, i.e., assuming an incomplete repair model. If we assume that the dose rate for radionuclide therapy, D(t), at a given time, t, can be expressed as an exponential expression:

$$\dot{D}(t) = \dot{D}_0 e^{-\lambda t} \quad (4),$$

Where $D_0$ is the initial dose rate and $\lambda$ is the effective clearance rate (=ln(2)/$t_e$; $t_e$=effective clearance half-life of the radiopharmaceutical), then, in the limit, as T approaches infinity, the integral in equation (3) reduces to:

$$\frac{\dot{D}_0^2}{2\lambda(\mu-\lambda)}. \quad (5)$$

Substituting this expression and replacing $D_T(T)$ with D, the total dose delivered, and using $D_0 = \lambda D$, which may be derived from equation (4), we get:

$$BED = D + \frac{\beta D^2}{\alpha}\left(\frac{\ln(2)}{\mu \cdot t_e + \ln(2)}\right). \quad (6)$$

In this expression, the effective clearance rate, $\lambda$, is represented by ln(2)/te. The derivation can be completed as discussed in the following references: Dale et al., *The Radiobiology of Conventional Radiotherapy and its Application to Radionuclide Therapy*, Cancer Biother Radiopharm (2005), Volume 20, Chapter 1, pages 47-51; Dale, *Use of the Linear-Quadratic Radiobiological Model for Quantifying Kidney Response in Targeted Tadiotherapy*, Cancer Biother Radiopharm, Volume 19, Issue 3, pages 363-370 (2004).

In cases where the kinetics in a particular voxel are not well fitted by a single decreasing exponential alternative, formalisms have been developed that account for an increase in the radioactivity concentration followed by exponential clearance. Since the number of imaging time-points typically collected in dosimetry studies would not resolve a dual parameter model (i.e., uptake and clearance rate), in one embodiment, the methodology assumes that the total dose contributed by the rising portion of a tissue or tumor time-activity curve is a small fraction of the total absorbed dose delivered.

Equation (6) depends upon the tissue-specific intrinsic parameters, $\alpha$, $\beta$ and $\mu$. These three parameters are set constant throughout a user-defined organ or tumor volume. The voxel specific parameters are the total dose in a given voxel and the effective clearance half-life assigned to the voxel. Given a voxel at coordinates (i,j,k), $D^{ijk}$ and $t_e^{ijk}$ are the dose and effective clearance half-life for the voxel. The imaging-based formulation of expression (6) that is incorporated into 3D-RD is then:

$$BED^{ijk} = D^{ijk} + \frac{\beta D^{ijk^2}}{\alpha}\left(\frac{\ln(2)}{\mu \cdot t_e^{ijk} + \ln(2)}\right). \quad (7)$$

The user inputs values of $\alpha$, $\beta$ and $\mu$ for a particular volume and $D^{ijk}$ and $t_e^{ijk}$ are obtained directly from the 3-D dose calculation and rate image, respectively. This approach requires organ or tumor segmentation that corresponds to the different $\alpha$, $\beta$ and $\mu$ values. The dose values are obtained by Monte Carlo calculation as described previously, and the effective clearance half-lives are obtained by fitting the data to a single exponential function. Once a spatial distribution of BED values has been obtained a dose-volume histogram of these values can be generated. Normalizing so that the total area under the BED (differential) DVH curve is one, converts the BED DVH to a probability distribution of BED values denoted, P($\Psi$), where $\Psi$ takes on all possible values of BED. Then, following the derivation for EUD as described in O'Donoghue's *Implications of Nonuniform Tumor Doses for Radioimmunotherapy*, J Nucl Med., Volume 40, Issue 8, pages 1337-1341 (1999), the EUD (1440) is obtained as:

$$EUD = -\frac{1}{\alpha}\ln\left(\int_0^\infty P(\psi)e^{-\alpha\psi}\,d\psi\right). \tag{8}$$

The EUD of the absorbed dose distribution (1465), as opposed to the BED distribution (1440), can also be obtained using equation (8), but using a normalized DVH of absorbed dose values rather than BED values. Expression (8) may be derived by determining the absorbed dose required to yield a surviving fraction equal to that arising from the probability distribution of dose values (absorbed dose or BED) given by the normalized DVH.

A rigorous application of equation (7) would require estimation of the absorbed dose at each time point (as in 1420); the resulting set of absorbed dose values for each voxel would then be used to estimate $t_c^{ijk}$ (1425). In using activity-based rate images to obtain the $t_e^{ijk}$, instead of the absorbed dose at each time point, the implicit assumption is being made that the local, voxel self-absorbed dose contribution is substantially greater than the cross-voxel contribution. This assumption avoids the need to estimate absorbed dose at multiple time-points, thereby substantially reducing the time required to perform the calculation. In another embodiment of the invention absorbed dose images at each time-point are generated and used for the BED calculation (1430), thereby avoiding the assumption regarding voxel self-dose vs cross-dose contribution.

Radiobiological Parameters for Clearance Rate Effect Example

The illustrative simplified examples and also the clinical implementation involve dose estimation to lungs and to a thyroid tumor. Values of α and β for lung, and the constant of repair, μ, for each tissue was taken from various sources. The parameter values are listed in the table in FIG. 21.

Clearance Rate Effect Example

As explained above, a sphere can be generated in a 563 matrix such that each voxel represents a volume of (0.15 cm)³. All elements with a centroid greater than 1 cm and less than or equal to (2.0 cm) ⅓ from the matrix center (at 28,28, 28) were given a clearance rate value (λ) corresponding to a half life of 2 hours. Those elements with a center position less than or equal to 1.0 cm from the center voxel were assigned a λ value equivalent to a 4 hour half life. In this way an outer shell (with 2 hour half life) was separated from an inner sphere (with 4 hour half life) (FIG. 23). This allowed both regions to have nearly equivalent volumes. The procedure was used to generate a matrix representing a sphere with a uniform absorbed dose distribution despite having non uniform clearance rate. This is accomplished by varying the initial activity such that the cumulative activity of both regions is identical. These two matrices were input into 3D-RD for the BED and EUD calculations. Input of a dose distribution rather than an activity distribution was necessary to make comparison with an analytical calculation possible. The partial-volume effects of a voxelized vs. idealized sphere were avoided by using the shell and sphere volumes obtained from the voxelized sphere rather than from a mathematical sphere. The impact of sphere voxelization on voxel-based MC calculations has been previously examined.

Absorbed Dose Distribution Effects. To demonstrate the impact of dose distribution on EUD, the following model was evaluated (FIG. 24). First, a uniform density sphere (1.04 g/cc in both regions) was evaluated with a uniform absorbed dose distribution of 10 Gy. Second, the uniform sphere was divided into two equal volume regions. The inner sphere was assigned zero absorbed dose while the outer shell was assigned an absorbed dose of 20 Gy. The effective half-life was 2 hours in both regions. Again the whole sphere average dose was 10 Gy.

Density Effects. To illustrate the effect of density differences, a sphere with radius 1.26 cm was created that had unit cumulated activity throughout, but a density of 2 g/cc in a central spherical region with radius 1 cm and 1 g/cc in the surrounding spherical shell (FIG. 25). The input parameters were chosen to yield a mean dose over the whole sphere of 10 Gy. Since, for a constant spatial distribution of energy deposition, the absorbed dose is a function of the density, the absorbed dose in the center is less than the absorbed dose of the shell. The distribution was selected so that the average over the two regions was 10 Gy. 3D-RD was used to generate a spatial distribution of absorbed dose values which were then used to estimate EUD over the whole sphere.

Application to a Patient Study

The 3D-RD dosimetry methodology was applied to an 11 year old female thyroid cancer patient who has been previously described in a publication on MCNP-based 3D-ID dosimetry.

Imaging. SPECT/CT images were obtained at 27, 74, and 147 hours post injection of a 37 MBq (1.0mCi) tracer 131I dose. All three SPECT/CT images focused on the chest of the patient and close attention was directed at aligning the patient identically for each image. The images were acquired with a GE Millennium VG Hawkeye system with a 1.59 cm thick crystal.

An OS-EM based reconstruction scheme was used to improve quantization of the activity map. A total of 10 iterations with 24 subsets per iteration was used. This reconstruction accounts for effects including attenuation, patient scatter, and collimator response. Collimator response includes septal penetration and scatter. The SPECT image counts were converted to units of activity by accounting for the detector efficiency and acquisition time. This quantification procedure, combined with image alignment, made it possible to follow the kinetics of each voxel. Using the CTs, which were acquired with each SPECT, each subsequent SPECT and CT image was aligned to the 27 hour 3-D image set. A voxel by voxel fit to an exponential expression was then applied to the aligned data set to obtain the clearance half-time for each voxel.

To obtain mean absorbed dose, mean BED and EUD, as well as absorbed dose and BED-volume-histograms, voxels were assigned to either tumor or normal lung parenchyma using an activity threshold of 21% of highest activity value.

Spherical Model Example

A spherical model was used to validate and illustrate the concepts of BED and EUD.

Clearance Rate Effects. Assuming that the sphere was lung tissue and applying the radiobiological parameters listed in the table of FIG. 21, the BED value in the slower clearing region, corresponding to the inner sphere with an activity clearance half-life of 4 hours, was 13.14 Gy. The faster clearing region (outer shell, 2 hr half-life) yielded a BED value of 15.69 Gy. The same model using the radiobiological values for tumor gave 10.09 Gy and 11.61 Gy for the slower clearing and faster clearing regions, respectively. The mean absorbed dose (AD) value for all these regions was 10 Gy.

Absorbed Dose Distribution Effects. The EUD value over the whole sphere when a uniform activity distribution was assumed recovered the mean absorbed dose of 10 Gy. A non-uniform absorbed dose distribution was applied such that the inner sphere was assigned an absorbed dose of zero, and an outer shell of equal volume, an absorbed dose of 20 Gy. In this case, the mean absorbed dose is 10 Gy, but the EUD was 1.83 Gy. The substantially lower EUD value is no longer a quantity that may be obtained strictly on physics principles, but rather is dependent on the applied biological model. The true absorbed dose has been adjusted to reflect the negligible probability of sterilizing all cells in a tumor volume when half of the tumor volume receives an absorbed dose of zero.

Density Effects. In the sphere with non-uniform density (inner sphere density of 2 g/cc, outer shell of equal volume (1 g/cc)) and an average absorbed dose of 10 Gy, the EUD over the whole sphere was 6.83 Gy. The EUD value is lower than the absorbed dose value to reflect the dose non-uniformity in spatial absorbed dose (inner sphere=5 Gy, outer shell=15 Gy) arising from the density differences.

Figure 26A:
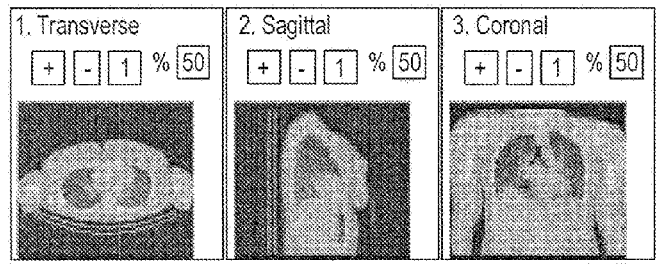
FIGS. 26A-D illustrate various image.
Figure 26B:
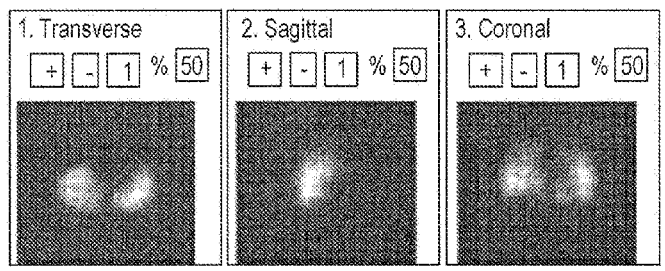
Figure 26C:
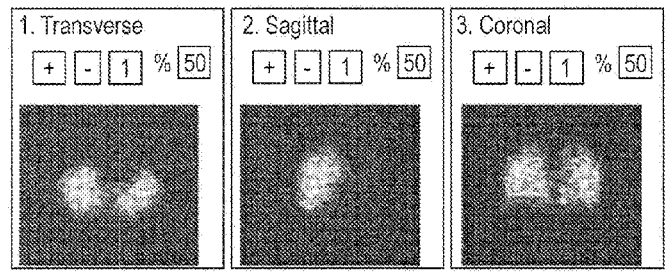
Figure 26D:
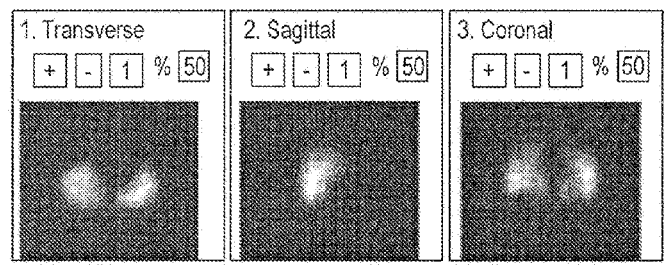

Application to a Patient Study. A 3D-RD calculation was performed for the clinical case described in the methods. A dosimetric analysis for this patient, without the radiobiological modeling described in this work has been previously published using the Monte Carlo code MCNP as opposed to EGSnrc which was used in this work. The clinical example illustrates all of the elements investigated using the simple spherical geometry. As shown on the CT scan (FIG. 26a), there is a highly variable density distribution in the lungs due to the tumor infiltration of normal lung parenchyma. Coupled with the low lung density, this gives a density and tissue composition that includes air, lung parenchyma and tumor (which was modeled as soft tissue). As shown on FIGS. 26b and 26c, the activity and clearance kinetics of 131I are also variable over the lung volume. These two data sets were used to calculate the cumulated activity images shown in FIG. 26d.

Figure 27:
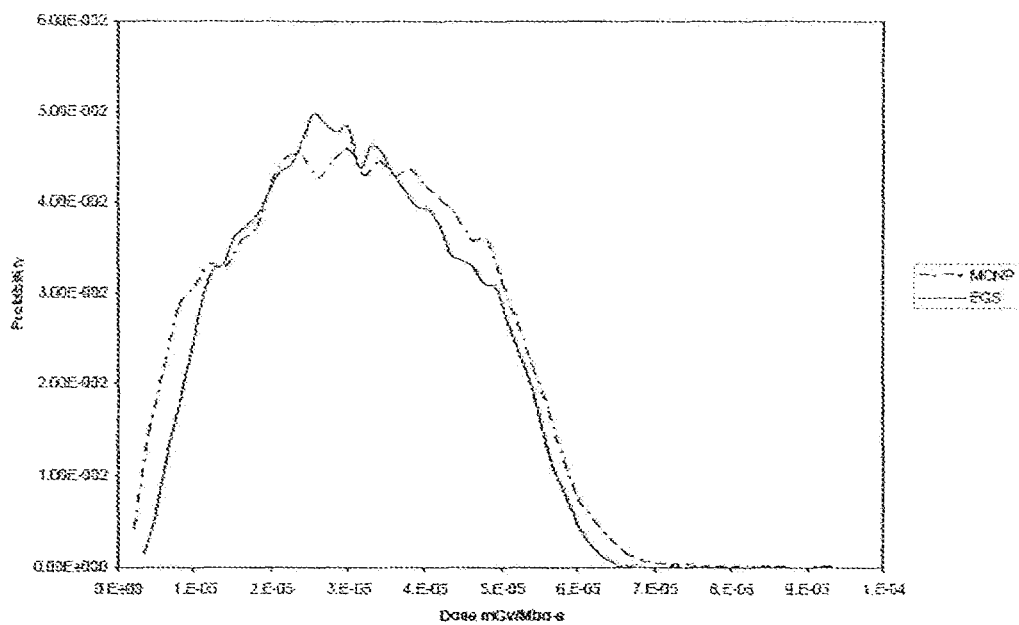
FIG. 27 depicts an example of the DVH of the absorbed dose distribution obtained with 3D-RD, according to one embodiment.

A comparison between the EGS-based 3D-RD calculation and the previously published MCNP-based calculation was performed. FIG. 27 depicts the DVH of the absorbed dose distribution obtained with 3D-RD superimposed on the same plot as the previously published DVH. Good overall agreement between the two DVHs is observed and the mean absorbed doses, expressed as absorbed dose per unit cumulated activity in the lung volume are in good agreement, $3.01 \times 10^{-5}$ and $2.88 \times 10^{-5}$ mGy/MBq-s per voxel, for the published, MCNP-based, and 3D-RD values, respectively.

Figure 28:
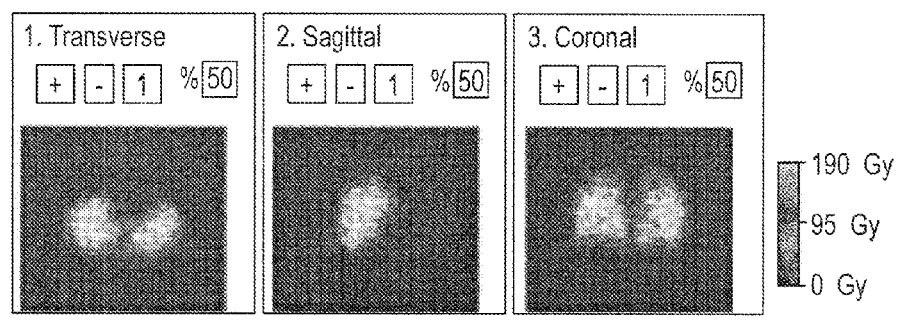
FIGS. 28 and 29 depict example results obtained with the radiobiological modeling capabilities of 3D-RD, according to several embodiments.
Figure 29:
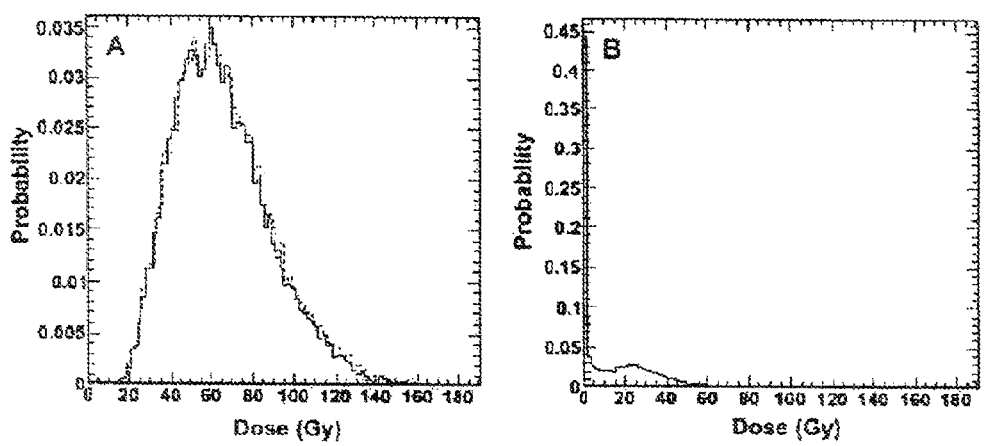

FIGS. 28 and 29 depict the results obtained with the radiobiological modeling capabilities of 3D-RD. FIG. 28 depicts a parametric image of BED values. Within this image the spotty areas of highest dose are areas where high activity and low density overlap. In FIG. 29a, normalized (so that the area under the curve is equal to 1) DVH and BED DVH (BVH) are shown for tumor voxels. The near superimposition of DVH and BVH suggests that dose rate will have a minimal impact on tumor response in this case. FIG. 29b depicts the normalized BVH for normal lung parenchyma. The DVH and BVH are given in Gy and reflect the predicted doses resulting from the administered therapeutic activity of 1.32 GBq (35.6 mCi) of 131I. These plots may be used to derive EUD values. It is important to note that the volume histograms must reflect the actual absorbed dose delivered and not the dose per unit administered activity. This is because the EUD is a nonlinear function of absorbed dose. The model relies on estimation of a tumor control probability to yield the equivalent uniform dose. If the data used to estimate EUD are expressed as dose per administered activity the EUD value will be incorrect. Mean absorbed dose, mean BED, and EUD are summarized in table 2. The EUD value for tumor, which accounts for the effect of a non-uniform dose distribution, was approximately 43% of the mean absorbed dose. This reduction brings the absorbed dose to a range that is not likely to lead to a complete response. The analysis demonstrates the impact of dose non-uniformity on the potential efficacy of a treatment.

Conclusion

While various embodiments have been described above, it should be understood that they have been presented by way of example, and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. Thus, the present embodiments should not be limited by any of the above described exemplary embodiments.

In addition, it should be understood that any figures which highlight the functionality and advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112, paragraph 6. Claims that do not expressly include the phrase "means for" or "step for" are not to be interpreted under 35 U.S.C. 112, paragraph 6.

The invention claimed is:

1. A method for determining absorbed dose information, comprising:
   a.) generating at least one anatomy image relating to anatomy of a particular patient using at least one tomography imaging device;
   b.) generating multiple radioactivity images regarding radioactivity distribution of an internally administered pharmaceutical over time in the particular patient using the at least one tomography imaging device;
   c.) registering the radioactivity images related to the radioactivity distribution over time;
   d.) combining each radioactivity image with each anatomy image to create activity images;
   d.) running a Monte Carlo simulation for each activity image to obtain absorbed dose-rate images of the pharmaceutical at multiple times;
   f.) integrating the absorbed dose-rate images over time to obtain a total absorbed dose image;
   g.) using the absorbed dose-rate images and-total absorbed dose image to obtain a biologically effective dose (BED) image; and
   h.) using the BED image to obtain an equivalent uniform dose (EUD) of BED values for a chosen anatomical region,
   wherein steps c.) through h.) are performed by a computer.

2. The method of claim 1, wherein the BED is depicted as a frequency of occurrence of a particular BED.

3. The method of claim 2, wherein the particular BED is depicted as:
   a differential BED histogram;
   an integral BED histogram; or
   iso BED contours over the image; or
   any combination thereof.

4. The method of claim 1, wherein a BED for each voxel is obtained from an individual voxel dose value and an individual voxel dose-rate parameter value or by a voxel dose-rate half-time value.

5. The method of claim 4, wherein the following equation is used to obtain the BED for each voxel given a voxel dose $D^{ijk}$, and a voxel dose-rate parameter value or the voxel dose-rate half-time $t_e^{ijk}$:

$$BED^{ijk} = D^{ijk} + \frac{\beta D^{ijk^2}}{\alpha}\left(\frac{\ln(2)}{\mu \cdot t_e^{ijk} + \ln(2)}\right). \quad (7)$$

6. The method of claim 1, further comprising combining each radioactivity image to generate a cumulative activity image; wherein the Monte Carlo is executed on a cumulative activity image to generate an absorbed dose image.

7. The method of claim 1, wherein the integrating is done analytically on a collection of data points represented by an equation.

8. The method of claim 1, wherein the integrating is done numerically on a collection of data points.

* * * * *